US010861151B2

(12) United States Patent
Liang et al.

(10) Patent No.: US 10,861,151 B2
(45) Date of Patent: Dec. 8, 2020

(54) METHODS, SYSTEMS, AND MEDIA FOR SIMULTANEOUSLY MONITORING COLONOSCOPIC VIDEO QUALITY AND DETECTING POLYPS IN COLONOSCOPY

(71) Applicants: Jianming Liang, Scottsdale, AZ (US); Nima Tajbakhsh, Tempe, AZ (US)

(72) Inventors: Jianming Liang, Scottsdale, AZ (US); Nima Tajbakhsh, Tempe, AZ (US)

(73) Assignee: THE ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 0 days.

(21) Appl. No.: 15/750,989

(22) PCT Filed: Aug. 8, 2016

(86) PCT No.: PCT/US2016/046055
§ 371 (c)(1),
(2) Date: Feb. 7, 2018

(87) PCT Pub. No.: WO2017/027475
PCT Pub. Date: Feb. 16, 2017

(65) Prior Publication Data
US 2018/0225820 A1    Aug. 9, 2018

Related U.S. Application Data

(60) Provisional application No. 62/202,565, filed on Aug. 7, 2015.

(51) Int. Cl.
*G06T 7/00* (2017.01)
*G06K 9/62* (2006.01)
(Continued)

(52) U.S. Cl.
CPC ........... *G06T 7/0012* (2013.01); *G06K 9/627* (2013.01); *G06K 9/6255* (2013.01);
(Continued)

(58) Field of Classification Search
USPC ........................................................ 382/128
See application file for complete search history.

(56) References Cited

U.S. PATENT DOCUMENTS 8,923,585 B1 * 12/2014 Peleg .................... G06T 7/0012
382/128
9,700,213 B2   7/2017 Tajbakhsh et al.
(Continued)

FOREIGN PATENT DOCUMENTS

KR       101386513 B1 *  4/2014
WO       2015031641 A1    3/2015
(Continued)

OTHER PUBLICATIONS

Van Wijk, C. et al., "Detection and Segmentation of Colonic Polyps on Implicit Isosurfaces by Second Principal Curvature Flow", IEEE Transactions on Medical Imaging, Mar. 2010, vol. 29, No. 3, pp. 688-698 <DOI:10.1109/TMI.2009.2031323>.
(Continued)

*Primary Examiner* — Amandeep Saini
(74) *Attorney, Agent, or Firm* — Elliott, Ostrander & Preston, P.C.

(57) ABSTRACT

Mechanisms for simultaneously monitoring colonoscopic video quality and detecting polyps in colonoscopy are provided. In some embodiments, the mechanisms can include a quality monitoring system that uses a first trained classifier to monitor image frames from a colonoscopic video to determine which image frames are informative frames and which image frames are non-informative frames. The informative image frames can be passed to an automatic
(Continued)

polyp detection system that uses a second trained classifier to localize and identify whether a polyp or any other suitable object is present in one or more of the informative image frames.

37 Claims, 23 Drawing Sheets

(51) Int. Cl.
    G16H 50/20        (2018.01)
    G16H 30/40        (2018.01)
    G06T 7/12         (2017.01)

(52) U.S. Cl.
    CPC .............. *G06K 9/6277* (2013.01); *G06T 7/12* (2017.01); *G16H 30/40* (2018.01); *G16H 50/20* (2018.01); *G06K 2209/053* (2013.01); *G06T 2207/10068* (2013.01); *G06T 2207/20072* (2013.01); *G06T 2207/20081* (2013.01); *G06T 2207/20084* (2013.01); *G06T 2207/30028* (2013.01); *G06T 2207/30032* (2013.01); *G06T 2207/30168* (2013.01)

(56) References Cited

U.S. PATENT DOCUMENTS

| | | |
|---|---|---|
| 9,741,116 B2 | 8/2017 | Liang et al. |
| 9,747,687 B2 | 8/2017 | Tajbakhsh et al. |
| 9,978,142 B2 | 5/2018 | Chi et al. |
| 10,052,027 B2 | 8/2018 | Tajbakhsh et al. |
| 10,055,843 B2 | 8/2018 | Tajbakhsh et al. |
| 2007/0078335 A1* | 4/2007 | Horn ............... A61B 1/041 600/425 |
| 2007/0213939 A1* | 9/2007 | Liew ............... C12Q 21/6886 702/20 |
| 2007/0273939 A1 | 9/2007 | Liew et al. |
| 2008/0194946 A1* | 8/2008 | Summers ......... A61B 5/7267 600/425 |
| 2013/0109915 A1 | 5/2013 | Krupnik et al. |
| 2013/0190600 A1* | 7/2013 | Gupta .............. A61B 8/0866 600/410 |
| 2017/0046835 A1* | 2/2017 | Tajbakhsh .......... G06T 7/73 |

FOREIGN PATENT DOCUMENTS

| | | | | |
|---|---|---|---|---|
| WO | WO-2015031641 A1 * | 3/2015 | ............... | G06T 5/20 |
| WO | WO-2015166675 A1 * | 11/2015 | ............. | H04N 5/232 |

OTHER PUBLICATIONS

Wang, Y. et al., "Part-Based Multiderivative Edge Cross-Sectional Profiles for Polyp Detection in Colonoscopy", IEEE Journal of Biomedical and Health Informatics, Jul. 2014, vol. 18, No. 4, pp. 1379-1389 <DOI:10.1109/JBHI.2013.2285230>.

Zhao, L. et al., "Lines of curvature for polyp detection in virtual colonoscopy", IEEE Transactions on Visualization and Computer Graphics, Sep./Oct. 2006, vol. 12, No. 5, pp. 885-892 <DOI:10.1109/TVCG.2006.158>.

Zhou, M. et al., "Polyp detection and radius measurement in small intestine using video capsule endoscopy", 7th International Conference on Biomedical Engineering and Informatics (Dalian, China, Oct. 14-16, 2014), 2014, pp. 237-241 <DOI:10.1109/BMEI.2014.7002777>.

Zhu, H. et al., "Improved curvature estimation for shape analysis in computer-aided detection of colonic polyps", Virtual Colonoscopy and Abdominal Imaging: Computational Challenges and Clinical Opportunities, 2011, vol. 6668, pp. 9-14 <DOI:10.1007/978-3-642-25719-3_2>.

Alexandre, L. et al., "Color and Position versus Texture Features for Endoscopic Polyp Detection", International Conference on BioMedical Engineering and Informatics (Sanya, China, May 27-30, 2008), 2008, vol. 2, pp. 38-42 <DOI:10.1109/BMEI.2008.246>.

Ameling, S. et al., "Texture-based polyp detectioin in colonoscopy", Bildverarbeitung Fr Die Medizin, 2009, pp. 346-350.

Atherton, T. et al., "Using phase to represent radius in the coherent circle Hough transform", IEE Colloquium Hough Transforms, 1993, pp. 1-5.

Bae, S. et al., "Polyp Detection via Imbalanced Learning and Discriminative Feature Learning", IEEE Transactions on Medical Imaging, Nov. 2015, vol. 34, No. 11, pp. 2379-2393 <DOI:10.1109/TMI.2015.2434398>.

Bernal, J. et al., "Impact of image preprocessing methods on polyp localization in colonoscopy frames", 35th Annual International Conference of the IEEE Engineering in Medicine and Biology Society (Osaka, Japan, Jul. 3-7, 2013), 2013, pp. 7350-7354 <DOI:10.1109/EMBC.2013.6611256>.

Bernal, J. et al., "Towards automatic polyp detection with a polyp appearance model", Pattern Recognition, Sep. 2012 [available online Mar. 2012], vol. 45, No. 9, pp. 3166-3182 <DOI:10.1016/j.patcog.2012.03.002>.

Bernal, J. et al., "Wm-dova maps for accurate polyp highlighting in colonoscopy: Validation vs. saliency maps from physicians", Computerized Medical Imaging and Graphics, Jul. 2015, vol. 43, pp. 99-111 <DOI:10.1016/j.compmedimag.2015.02.007>.

Cheng, D. et al., "Automatic detection of colorectal polyps in static images", Biomedical Engineering: Applications, Basis and Communications, 2011, vol. 23, No. 5, pp. 357-367 <DOI:10.4015/S1016237211002761>.

Dalal, N. et al., "Histograms of oriented gradients for human detection", IEEE Computer Society Conference on Computer Vision and Pattern Recognition (San Diego, CA, Jun. 20-25, 2005), 2005, vol. 1, pp. 886-893 <DOI:10.1109/CVPR.2005.177>.

Figueiredo, I. et al., "An intelligent system for polyp detection in wireless capsule endoscopy images", Thematic Conferences on Computational Vision and Medical Image Processing, Oct. 2013, pp. 229 <DOI:10.1201/b15810-42>.

Godec, M. et al., "Hough-Based Tracking of Deformable Objects", in: Crimisi, A. et al., "Decision Forests for Computer Vision and Medical Image Analysis" (Springer 2013), pp. 159-173.

Gross, S. et al., "Automated classification of colon polyps in endoscopic image data", Proceedings of SPIE, Feb. 2012, vol. 8315, article 83150W, 8 pages <DOI:10.1117/12.911177>.

Heresbach, D. et al., "Miss rate for colorectal neoplastic polyps: a prospective multicenter study of back-to-back video colonoscopies", Endoscopy, Apr. 2008, vol. 40, No. 4, pp. 284-290 <DOI:10.1055/s-2007-995618>.

Hwang, S. et al., "Polyp detection in colonoscopy video using elliptical shape feature", IEEE International Conference on Image Processing (San Antonio, TX, Sep. 16-Oct. 19, 2007), 2007, vol. 2, pp. II-465-II-468 <DOI:10.1109/ICIP.2007.4379193>.

Hwang, S. et al., "Polyp detection in wireless capsule endoscopy videos based on image segmentation and geometric feature", IEEE International Conference on Acoustics, Speech and Signal Processing (Dallas, TX, Mar. 14-19, 2010), 2010, pp. 678-681 <DOI:10.1109/ICASSP.2010.5495103>.

Iakovidis, D. et al., "A comparative study of texture features for the discrimination of gastric polyps in endoscopic video", IEEE Symposium on Computer-Based Medical Systems (Dublin, Ireland, Jun. 23-24, 2005), 2005, pp. 575-580 <DOI:10.1109/CBMS.2005.6>.

Karkanis, S. et al., "Computer-aided tumor detection in endoscopic video using color wavelet features", IEEE Transactions on Information Technology in Biomedicine, Sep. 2003, vol. 7, No. 3, pp. 141-152 <DOI:10.1109/TITB.2003.813794>.

Kim, D. et al., "CT Colonography versus Colonoscopy for the Detection of Advanced Neoplasia", New England Journal of Medicine, Oct. 2007, vol. 357, No. 14, pp. 1403-1412 <DOI:10.1056/NEJMoa070543>.

Kwitt, R. et al., "Learning pit pattern concepts for gastroenterological training", Medical Image Computing and Computer-Assisted Intervention, 2011, vol. 6893, pp. 280-287 <DOI:10.1007/978-3-642-23626-6_35>.

(56) References Cited

OTHER PUBLICATIONS

Lee, J. et al., "A straightforward approach to computer-aided polyp detection using a polyp-specific volumetric feature in colonography", Computers in Biology and Medicine, Sep. 2011, vol. 41, No. 9, pp. 790-801 <DOI:10.1016/j.compbiomed.2011.06.015>.
Leufkens, A. et al., "Factors influencing the miss rate of polyps in a back-to-back colonoscopy study", Endoscopy, May 2012, vol. 44, No. 5, pp. 470-475 <DOI:10.1055/s-0031-1291666>.
Li, B.et al., "Automatic polyp detection for wireless capsule endoscopy images", Expert Systems with Applications, Sep. 2012, vol. 39, No. 12, pp. 10952-10958 <DOI:10.1016/j.eswa.2012.03.029>.
Lieberman, D., "Quality and colonoscopy: A new imperative", Gastrointestinal Endoscopy, Mar. 2005, vol. 61, No. 3, pp. 392-394 <DOI:10.1016/S0016-5107(05)00133-1>.
Machine Vision Group, "CVC colon DB" [online], Autonomous University of Barcelona, 2010-2013 [retrived on Apr. 30, 2019 from archive.org, as it appeared on Jun. 14, 2013], retrieved from the internet: <URL:https://web.archive.org/web/20130614204845/http://mv.cvc.uab.es/projects/colon-qa/cvccolondb>.
Mamonov, A. et al., "Automated polyp detection in colon capsule endoscopy", IEEE Transactions on Medical Imaging, Jul. 2014, vol. 33, No. 7, pp. 1488-1502 <DOI:10.1109/TMI.2014.2314959>.
McGill, R. et al., "Variations of box plots", The American Statistician, Feb. 1978, vol. 32, No. 1, pp. 12-16 <DOI:10.2307/2683468>.
Montillo, A. et al., "Entanglement and Differentiable Information Gain Maximization", in: Crimisi, A. et al., "Decision Forests for Computer Vision and Medical Image Analysis" (Springer 2013), pp. 273-293.
Mordohai, P. et al., "Tensor Voting: A Perceptual Organization Approach to Computer Vision and Machine Learning", Synthesis Lectures on Image, Video, and Multimedia Processing, 2006, 136 pages.
Oh, J. et al., "Measuring objective quality of colonoscopy", IEEE Transactions on Biomedical Engineering, Sep. 2009, vol. 56, No. 9, pp. 2190-2196 <DOI:10.1109/TBME.2008.2006035>.
Ojala, T. et al., "Multiresolution gray-scale and rotation invariant texture classification with local binary patterns", IEEE Transactions on Pattern Analysis and Machine Intelligence, Jul. 2002, vol. 24, No. 7, pp. 971-987 <DOI:10.1109/TPAMI.2002.1017623>.
Ong, J. et al., "From Point to Local Neighborhood: Polyp Detection in CT Colonography Using Geodesic Ring Neighborhoods", IEEE Transactions on Image Processing, Apr. 2011, vol. 20, No. 4, pp. 1000-1010 <DOI:10.1109/TIP.2010.2076295>.
Pabby, A. et al., "Analysis of colorectal cancer occurrence during surveillance colonoscopy in the dietary Polyp Prevention Trial", Gastrointestinal Endoscopy, Mar. 2005, vol. 61, No. 3, pp. 385-391 <DOI:10.1016/S0016-5107(04)02765-8>.
Park, S. et al., "A colon video analysis framework for polyp detection", IEEE Transactions on Biomedical Engineering, May 2012, vol. 59, No. 5, pp. 1408-1418 <DOI:10.1109/TBME.2012.2188397>.
Patent Cooperation Treaty, International Searching Authority, International Preliminary Report on Patentability and Written Opinion for PCT/US2016/046055, 5 pages.
Patent Cooperation Treaty, International Searching Authority, International Search Report for PCT/US2016/046055, 2 pages.
Rabeneck, L. et al., "Outcomes of Colorectal Cancer in the United States: No Change in Survival (1986-1997)", American Journal of Gastroenterology, Feb. 2003, vol. 98, No. 2, pp. 471-477 <DOI:10.1111/i.1572-0241.2003.07260.x>.

Siegel, R. et al., "Cancer Statistics, 2015", CA: A Cancer Journal for Clinicians, Jan./Feb. 2015, vol. 65, No. 1, pp. 5-29 <DOI:10.3322/caac.21254>.
Silva, J. et al., "Toward embedded detection of polyps in WCE images for early diagnosis of colorectal cancer", International Journal of Computer Assisted Radiology and Surgery, Mar. 2014, vol. 9, No. 2, pp. 283-293 <DOI:10.1007/s11548-013-0926-3>.
Suzuki, K. et al., "Massive-training artificial neural network coupled with laplacian-eigenfunction-based dimensionality reduction for computer-aided detection of polyps in ct colonography", IEEE Transactions on Medical Imaging, Nov. 2010, vol. 29, No. 11, pp. 1907-1917 <DOI:10.1109/TMI.2010.2053213>.
Tajbakhsh, N. et al., "A Classification-Enhanced Vote Accumulation Scheme for Detecting Colonic Polyps", Abdominal Imaging Computation and Clinical Applications, Sep. 2013, vol. 8198, pp. 53-62.
Tajbakhsh, N. et al., "A comprehensive computer-aided polyp detection system for colonoscopy videos", Information Processing in Medical Imaging, 2015 [available online Jun. 2015], vol. 24, pp. 327-338 <DOI:10.1007/978-3-319-19992-4 25>.
Tajbakhsh, N. et al., "Automated Polyp Detection in Colonoscopy Videos Using Shape and Context Information", IEEE Transactions on Medical Imaging, Feb. 2016 [available online Oct. 2015], vol. 35, No. 2, pp. 630-644 <DOI:10.1109/TMI.2015.2487997>.
Tajbakhsh, N. et al., "Automatic assessment of image informativeness in colonoscopy", International Workshop on Computational and Clinical Challenges in Abdominal Imaging, Dec. 2014, vol. 8676, pp. 151-158 <DOI:10.1007/978-3-319-13692-9>.
Tajbakhsh, N. et al., "Automatic polyp detection from learned boundaries", IEEE 11th International Symposium on Biomedical Imaging (Beijing, China, Apr. 29-May 2, 2014), 2014, pp. 97-100 <DOI:10.1109/ISBI.2014.6867818>.
Tajbakhsh, N. et al., "Automatic polyp detection in colonoscopy videos using an ensemble of convolutional neural networks", IEEE 12th International Symposium on Biomedical Imaging (New York, NY, Apr. 16-19, 2015), 2015, pp. 79-83 <DOI:10.1109/ISBI.2015.7163821>.
Tajbakhsh, N. et al., "Automatic Polyp Detection Using Global Geometric Constraints and Local Intensity Variation Patterns", International Conference on Medical Image Computing and Computer-Assisted Intervention, 2014, vol. 8674, pp. 179-187.
Tamaki, T. et al., "Computer-aided colorectal tumor classification in endoscopy using local features", Medical Image Analysis, Jan. 2013, vol. 17, No. 1, pp. 78-100 <DOI:10.1016/j.media.2012.08.003>.
Tola, E. et al., "DAISY: An efficient dense descriptor applied to wide baseline stereo", IEEE Transactions on Pattern Analysis and Machine Intelligence, May 2010, vol. 32, No. 5, pp. 815-830 <DOI:10.1109/TPAMI.2009.77>.
Van Ravesteijn, V. et al., "Computer-Aided Detection of Polyps in CT Colonography Using Logistic Regression", IEEE Transactions on Medical Imaging, Jan. 2010, vol. 29, No. 1, pp. 120-131 <DOI:10.1109/TM1.2009.2028576>.
Van Rijn, J. et al., "Polyp miss rate determined by tandem colonoscopy: a systematic review", The American Journal of Gastroenterology, Feb. 2006, vol. 101, No. 2, pp. 343-350 <DOI:10.1111/j.1572-0241.2006.00390.x>.
International Preliminary Report on Patentability dated Feb. 22, 2018 in International Patent Application No. PCT/US2016/046055.
International Search Report and Written Opinion dated Oct. 26, 2016 in International Patent Application No. PCT/US2016/046055.

* cited by examiner

| Number of Clusters | Number of Sampled Points | | | | |
|---|---|---|---|---|---|
| | 50 | 150 | 200 | 250 | 1000 |
| 5 | 0.7748 | 0.7881 | 0.8119 | 0.8181 | 0.8633 |
| 10 | 0.8098 | 0.8841 | 0.8774 | 0.8919 | 0.9238 |
| 15 | 0.8193 | 0.8815 | 0.8737 | 0.8816 | 0.9257 |
| 20 | 0.8687 | 0.9091 | 0.9067 | 0.9145 | 0.9393 |
| 25 | 0.8653 | 0.9069 | 0.9122 | 0.9247 | 0.9412 |
| 50 | 0.8781 | 0.9144 | 0.9180 | 0.9280 | 0.9403 |
| 100 | 0.8961 | 0.9165 | 0.9284 | 0.9378 | 0.9483 |
| 150 | 0.9017 | 0.8915 | 0.9296 | 0.9382 | 0.9500 |
| 200 | 0.8951 | 0.9268 | 0.9341 | 0.9384 | 0.9518 |
| 250 | 0.9190 | 0.9246 | 0.9321 | 0.9384 | 0.9602 |

TRAINING IMAGE 1 (710)
LABEL: Y=0

TRAINING IMAGE 2 (720)
LABEL: Y=1

TRAINING IMAGE 3 (730)
LABEL: Y=1

↑
DIVIDE EACH IMAGE
INTO N PATCHES
(810)

TRAINING IMAGE 1 (710)

METHODS, SYSTEMS, AND MEDIA FOR SIMULTANEOUSLY MONITORING COLONOSCOPIC VIDEO QUALITY AND DETECTING POLYPS IN COLONOSCOPY

CROSS-REFERENCE TO RELATED APPLICATIONS

This application claims the benefit of U.S. Provisional Patent Application No. 62/202,565, filed Aug. 7, 2015, which is hereby incorporated by reference herein in its entirety.

TECHNICAL FIELD

The disclosed subject matter relates to methods, systems, and media for simultaneously monitoring colonoscopic video quality and detecting polyps in colonoscopy. More particularly, the disclosed subject matter relates to implementing a quality monitor that can be used to determine video quality and the informativeness of one or more images in the colonoscopic video and implementing a polyp detector that can automatically determine whether a polyp may be present in one or more informative images from the colonoscopic video.

BACKGROUND

Colorectal cancer is the third leading cause of cancer-related deaths in the United States. Prior to reaching a cancerous stage, colorectal cancer most often begins in the form of small polyps, adenomas, or abnormal growths of the colon surface that, when found early, may be easily and safely removed. The preferred screening technique for polyp detection and removal is optical colonoscopy, during which a scope with an attached camera is inserted and guided through the colon to meticulously examine the colon wall to find polyps for removal. Despite many screening and therapeutic advantages, polyp detection with optical colonoscopy remains a challenging task and as evidenced by a recent clinical study, where 22% of polyps remained undetected during colon screening with optical colonoscopy. Similar polyp miss rates have also been reported by other clinical studies. To compound the problem, between 4% to 6% of the colorectal cancers diagnosed are thought to be missed on prior colonoscopy. Because this procedure generally relies on the attentiveness of the endoscopist or medical professional for identifying polyps, these high miss rates may be attributed to poor diligence or navigational skills for maneuvering the scope. Poor diligence can, unfortunately, result in a hasty examination, while substandard navigational skills can imply poor visualization of the colon. It is therefore important to reduce polyp miss rate as it decreases the incidence and mortality of colorectal cancer.

Computer-aided polyp detection has recently been considered as a tool for reducing polyp miss-rate, where the idea is to highlight regions with suspected polyps during a colonoscopy procedure. Existing techniques for automatic polyp detection have, thus far, primarily relied upon texture or shape information for detecting polyps. Although texture is a distinguishing characteristic of polyps, merely relying on texture may not address the automatic detection problem. For example, the texture of a polyp becomes fully visible only if the camera captures close shots of the surface of a polyp. This condition is often met when polyps have already been detected by operators, which obviously eliminates the need for computer-aided detection. On the other hand, shape information cannot be considered as a reliable measure since polyps appear in a variety of forms ranging from sessile to peduncular shapes.

Accordingly, it is desirable to provide methods, systems, and media for simultaneously monitoring colonoscopic video quality and detecting polyps in colonoscopy that overcome these and other deficiencies of the prior art.

SUMMARY

Mechanisms for simultaneously monitoring colonoscopic video quality and detecting polyps in colonoscopy are provided.

In accordance with some embodiments of the disclosed subject matter, a method for polyp detection in optical colonoscopic images is provided, the method comprising: receiving a plurality of image frames of a colonoscopic video; applying, using a hardware processor, a first trained classifier to each image frame of the plurality of image frames, wherein the first trained classifier determines an informativeness score that indicates a likelihood that an image frame includes informative content; presenting an interface that includes an image frame from the plurality of images, wherein the interface includes an indicator that represents the informativeness score of the image in the interface; determining whether each image frame from the plurality of image frames is an informative image frame based on the informativeness score; applying a second trained classifier to each informative image frame, wherein the second trained classifier determines a polyp detection scores that indicates a likelihood that the informative image frame contains one or more polyps; and presenting, in the interface, an indication that a polyp has been detected in the informative image frame.

In some embodiments, the first trained classifier is a random forest classifier that is trained based on extracted features from training images and clustering the extracted features to form visual words based on a bag of visual words model.

In some embodiments, the first trained classifier is a random forest classifier that is constructed based on histograms that represent the number of features belonging to each visual words in a bag of visual words model.

In some embodiments, the first trained classifier is a convolutional neural network classifier, wherein the convolutional neural network classifier divides the image frame into a plurality of regions, applies the convolutional neural network classifier to each of the plurality of regions to obtain a plurality of informativeness scores, aggregates the plurality of informativeness scores to obtain an aggregate informativeness score, and labels the image frame based on the aggregated informativeness score.

In some embodiments, the method further comprises: applying a third trained classifier to each informative image frame to classify which pixels in an informative image frame are likely to contain a polyp edge; and generating an edge map based on the polyp edge classification information.

In some embodiments, a Canny edge detector is applied to each informative image frame to obtain a Canny edge map and wherein the generated edge map includes common pixels between the Canny edge map and a ground truth image corresponding to the informative image frame.

In some embodiments, the method further comprises: applying a Hough transform to the generated edge map to obtain a plurality of candidate polyps; extracting image patches from the plurality of candidate polyps; applying the second trained classifier to the extracted image patches, wherein the second trained classifier is a convolutional neural network classifier that classifies each of the extracted image patches to obtain a plurality of polyp classification scores; aggregating the plurality of polyp classification scores to obtain an aggregate polyp score; and labeling the informative image frame based on the aggregated polyp score.

In some embodiments, the method further comprises presenting a second indicator in the interface that represents an average informativeness score over a subset of image frames.

In some embodiments, presenting the indication further comprises placing a bounding box in an area surrounding the detected polyp.

In accordance with some embodiments of the disclosed subject matter, a system for polyp detection in optical colonoscopic images is provided, the system comprising a hardware processor that is configured to: receive a plurality of image frames of a colonoscopic video; apply a first trained classifier to each image frame of the plurality of image frames, wherein the first trained classifier determines an informativeness score that indicates a likelihood that an image frame includes informative content; present an interface that includes an image frame from the plurality of images, wherein the interface includes an indicator that represents the informativeness score of the image in the interface; determine whether each image frame from the plurality of image frames is an informative image frame based on the informativeness score; apply a second trained classifier to each informative image frame, wherein the second trained classifier determines a polyp detection scores that indicates a likelihood that the informative image frame contains one or more polyps; and present, in the interface, an indication that a polyp has been detected in the informative image frame.

In accordance with some embodiments of the disclosed subject matter, a non-transitory computer-readable medium containing computer-executable instructions that, when executed by a processor, cause the processor to perform a method for polyp detection in optical colonoscopic images is provided, the method comprising: receiving a plurality of image frames of a colonoscopic video; applying a first trained classifier to each image frame of the plurality of image frames, wherein the first trained classifier determines an informativeness score that indicates a likelihood that an image frame includes informative content; presenting an interface that includes an image frame from the plurality of images, wherein the interface includes an indicator that represents the informativeness score of the image in the interface; determining whether each image frame from the plurality of image frames is an informative image frame based on the informativeness score; applying a second trained classifier to each informative image frame, wherein the second trained classifier determines a polyp detection scores that indicates a likelihood that the informative image frame contains one or more polyps; and presenting, in the interface, an indication that a polyp has been detected in the informative image frame.

In accordance with some embodiments of the disclosed subject matter, a system for polyp detection in optical colonoscopic images is provided, the system comprising: means for receiving a plurality of image frames of a colonoscopic video; means for applying a first trained classifier to each image frame of the plurality of image frames, wherein the first trained classifier determines an informativeness score that indicates a likelihood that an image frame includes informative content; means for presenting an interface that includes an image frame from the plurality of images, wherein the interface includes an indicator that represents the informativeness score of the image in the interface; means for determining whether each image frame from the plurality of image frames is an informative image frame based on the informativeness score; means for applying a second trained classifier to each informative image frame, wherein the second trained classifier determines a polyp detection scores that indicates a likelihood that the informative image frame contains one or more polyps; and means for presenting, in the interface, an indication that a polyp has been detected in the informative image frame.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

Figure 1A:
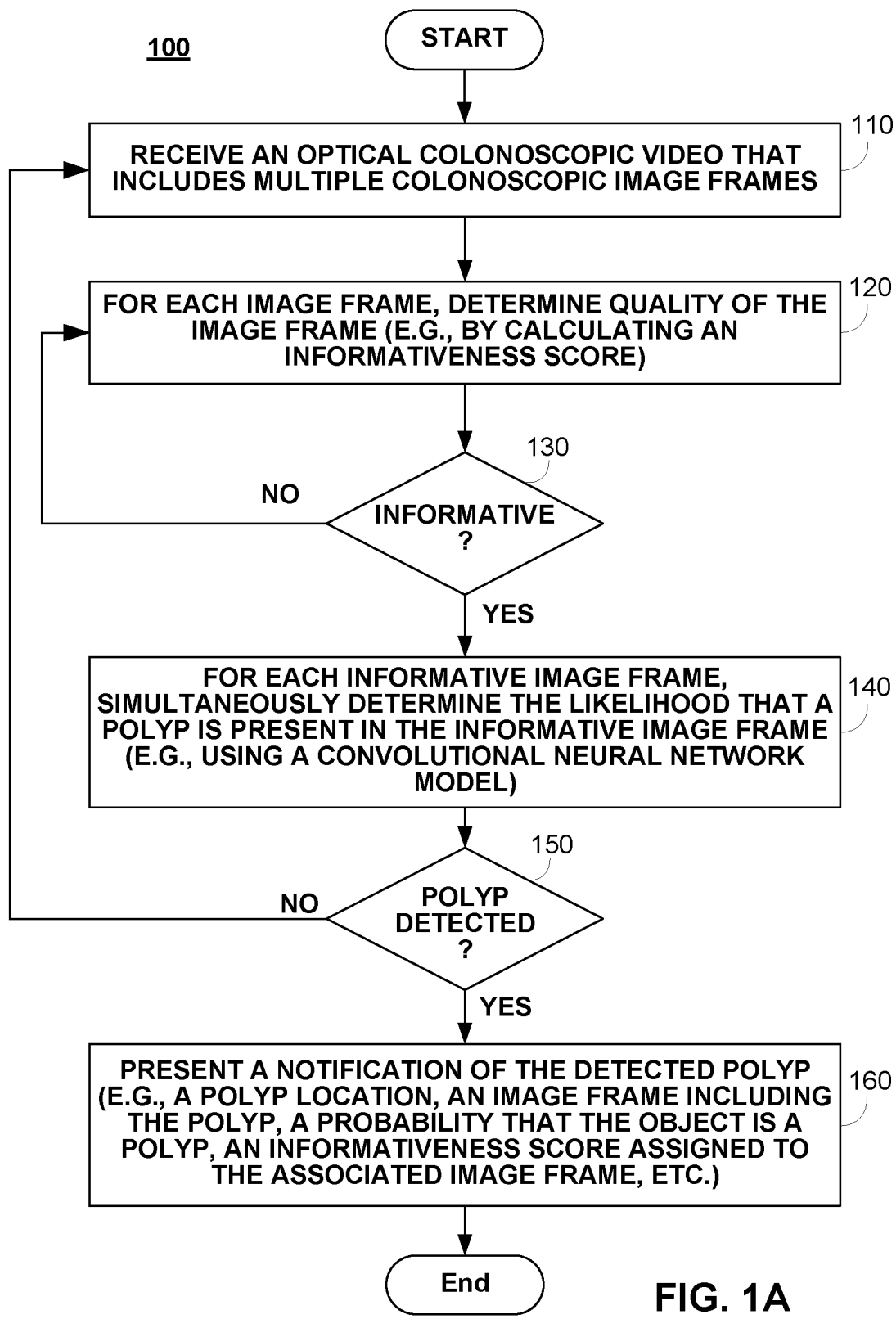
FIG. 1A is an illustrative example of a process for simultaneously monitoring colonoscopic video quality and detecting polyps in colonoscopy in accordance with some embodiments of the disclosed subject matter.

In accordance with some embodiments of the disclosed subject matter, mechanisms for simultaneously monitoring colonoscopic video quality and detecting polyps in colonoscopy are provided.

In some embodiments, the mechanisms can include a quality monitor that monitors image frames from a colonoscopic video to determine which image frames are informative frames and which image frames are non-informative frames. Generally speaking, informative frames can include images that are in-focus, thereby providing the ability to see portions of the colon and polyps with sufficient clarity with high levels of information content throughout the image frames. On the other hand, non-informative frames can include images that may be blurred due to a rushed colonoscopic examination, images that may be partially obscured or dark from wall content (e.g., due to poor navigational skills when maneuvering the scope during a colonoscopy), etc.

It should be noted that the quality monitor can classify image frames within a colonoscopic video as being informative or non-informative using any suitable machine learning approach. For example, the quality monitor can extract features from images and cluster the extracted features to form visual words based on a bag of visual words model. A histogram can then be constructed for each image that represents the number of features belonging to each visual word and a random forest model can be constructed based on the histograms associated with each image. In another example, the quality monitor can implement a convolutional neural network classifier for classifying image frames within a colonoscopic video as being informative or non-informative.

In some embodiments, the mechanisms can be used to provide an indication of informative frames and/or an indication of non-informative frames. For example, in response to detecting the presence of non-informative frames in a colonoscopic video during a colonoscopy procedure, the mechanisms can provide an alert or other notification to an endoscopist or medical processional of the quality of the images in the colonoscopic video. This can, for example, result in re-examining the past segment of the colon and also can, for example, improve the diligence of the endoscopist during the colonoscopy procedure and, in turn, increase the quality of the examination and lower polyp miss rates.

In another example, in response to detecting one or more informative frames in a colonoscopic video, the mechanisms can transmit the informative frames to a polyp detector that simultaneously detects whether a polyp, a polyp-like structure, or any other suitable object is present in the one or more informative frames.

In some embodiments, the mechanisms can include a polyp monitor that detects polyps in image frames from a colonoscopic video using machine learning techniques to localize and identify polyps. For example, the polyp detector can identify polyp edges or boundaries by extracting features from pixels and passing these features to a random forest classification model for distinguishing between polyp edges and non-polyp edges. Based on this classification, polyps can be detected by applying a Hough transform on refined edge maps reconstructed from the random forest classifications. The detected circles from the Hough transform can serve as the basis for constructing patches from each images, which can then be passed to a convolutional neural network classifier for classification as being a polyp or a non-polyp.

In some embodiments, the mechanisms can be used to provide an indication of the presence of a detected polyp in an informative frame. For example, in response to determining that the probability that an informative frame contains a polyp is greater than a predetermined probabilistic threshold, the mechanisms can present the informative image frame along with a bounding box or other indication of the detected polyp within the informative image frame. In another example, the informative image frame with the detected polyp can be presented with any suitable information, such as a quality score for the image frame, a polyp probability score, polyp location information, image frame information, video information, polyp shape information, polyp size information, polyp color information, etc. This can, for example, direct the attention of the endoscopist towards polyps, thus increasing endoscopist attentiveness and reducing polyp miss rates.

As used herein, the term "image" may refer to multi-dimensional data composed of discrete image elements (e.g., pixels for two-dimensional images and voxels for three-dimensional images). The image may be, for example, a medical image of a subject collected using an optical colonoscopy system, a capsule endoscopy system, a computer tomography system, a magnetic resonance imaging system, an ultrasound imaging system, or any other medical imaging system or imaging modality known to one of skill in the art. The image may also be provided from non-medical contexts, such as, for example, remote sensing systems, electron microscopy systems, etc. Although an image can be thought of as a function from R3 to R, the methods of the disclosed subject matter are not limited to such images, and can be applied to images of any dimension, e.g., a two-dimensional picture, a three-dimensional volume, or a four-dimensional space. For a two-dimensional or three-dimensional image, the domain of the image is typically a two-dimensional or three-dimensional rectangular array, where each pixel or voxel can be addressed with reference to a set of two or three mutually orthogonal axes. Additionally or alternatively, the methods of the disclosed subject matter can be applied to images of any color, any depth, etc.

These and other features for simultaneously monitoring colonoscopic video quality and detecting polyps in colonoscopy are described in connection with FIGS. 1A-26.

Turning to FIG. 1A, FIG. 1A shows an illustrative example of a process 100 for simultaneously monitoring colonoscopic video quality and detecting polyps in colonoscopy in accordance with some embodiments of the disclosed subject matter.

At 110, process 100 can begin by receiving an optical colonoscopic video that includes multiple colonoscopic image frames. For example, an optical colonoscopy system can be connected to image acquisition hardware, which acquires optical image data continuously or intermittently during a medical procedure, such as a colonoscopy, and transmit optical image data for processing. It should be noted that the image acquisition hardware may require operator direction, input or feedback, or may be configured to operate autonomously. In a more particular example, the image acquisition hardware that is connected to the optical colonoscopy system can be configured to obtain an optical colonoscopic video, where the image acquisition hardware can convert the colonoscopic video into multiple image frames or otherwise generate the image frames from the colonoscopic video (e.g., a live feed). It should be noted that, in some embodiments, the image frames can be stored in a storage device, such as a memory, for retrieval and analysis by the quality monitor system and/or the polyp detection system described herein.

Process 100 can continue, at 120, by assessing each image frame to determine colonoscopy image informativeness or quality. For example, an image frame from the colonoscopic video can be assessed and a machine learning technique can be applied that determines a probability of whether the image frame is an informative frame or a non-informative frame. Generally speaking, an informative frame can include an image that is in-focus and can include a high level of informational content, thereby providing an endoscopist with the ability to see portions of the colon and polyps with sufficient clarity. An example of an informative frame may be where the information content is well-spread over the image. On the other hand, a non-informative frame can include an image that is out-of-focus with one or more bubbles in the image, an image captured during wall contact with light reflection artifacts, an image that is motion blurred due to wall contact, an image that is motion blurred due to a rushed colonoscopic examination, etc.

In some embodiments, this can include using a machine learning technique to assign a quality or informativeness score. For example, the quality monitor can extract features from images and cluster the extracted features to form visual words based on a bag of visual words model. A histogram can then be constructed for each image that represents the number of features belonging to each visual word and a random forest model can be constructed based on the histograms associated with each image. In another example, the quality monitor can implement a convolutional neural network classifier for classifying image frames within a colonoscopic video as being informative or non-informative.

By monitoring the informativeness scores during a procedure, such as a colonoscopy, an alert, a notification, or a visual indicator can be presented to the endoscopist or user performing the procedure. For example, in response to detecting the presence of non-informative frames in a colonoscopic video during a colonoscopy procedure, an alert or other notification can be presented to an endoscopist of the quality of the images in the colonoscopic video. This can, for example, result in re-examining the past segment of the colon and also can, for example, improve the diligence of the endoscopist during the colonoscopy procedure and, in turn, increase the quality of the examination and lower polyp miss rates.

Figure 1B:
FIG. 1B is an illustrative example of an interface that includes indications of video quality (e.g., a current quality indicator and an average quality indicator over a period of time) in accordance with some embodiments of the disclosed subject matter.

For example, as shown in FIG. 1B, a bar indicator 172 can provide an indication of the informativeness of an image frame 170 from a colonoscopic video. As also shown in FIG. 1B, a traffic light indicator 174 can provide an indication of the informativeness over time (e.g., informativeness over the last three seconds). In an illustrative example of traffic light indicator 174, a green light can indicate that a significant number of image frames includes informative frames, a yellow light can indicate that a given number of non-informative image frames has been detected (e.g., greater than a threshold value, a number of consecutive non-informative image frames, etc.), and a red light can indicate that a significant number of image frames include non-informative frames (e.g., greater than a second threshold value, a greater number of consecutive non-informative image frames, etc.). In a more particular example, the lights in traffic light indicator 174 can be correlated with the average of informativeness scores for a particular number of image frames over a particular period of time. Traffic light indicator 174 can, for example, alert the user performing the procedure of the onset of a hasty or low quality colon examination.

Referring back to FIG. 1A, process 100 can, at 130, determine whether the image frame is informative or not based on the informativeness score. In response to determining that the image frame from the colonoscopic video is deemed to be informative (e.g., the informativeness score associated with that image frame is greater than a threshold informativeness value), process 100 can proceed to step 140, where additional detections, such as the presence of polyps, can be made in connection with the informative image frame (e.g., by the automatic polyp detection system). Alternatively, in response to determining that the image frame is not deemed to be informative, process 100 can return to step 120, where the quality monitor system can process the next image frame.

In some embodiments, upon determining which image frames from the colonoscopic video are deemed informative (e.g., having an informativeness score or any other suitable probability greater than a threshold value), these image frames can be transmitted to a polyp detection system for simultaneously determining the likelihood that a polyp is present in an informative image frame at 140. For example, an informative image frame can be transmitted to a polyp detection system that determines the probability that a polyp is present using machine learning techniques to localize and identify polyps. In a more particular example, the polyp detection system can identify polyp edges or boundaries by extracting features from pixels and passing these features to a random forest classification model for distinguishing between polyp edges and non-polyp edges. Based on this classification, a polyp can be detected by applying a Hough transform on refined edge maps reconstructed from the random forest classifications. The detected circles from the Hough transform can serve as the basis for constructing patches from each images, which can then be passed to a convolutional neural network classifier for classification as being a polyp or a non-polyp.

Figure 1C:
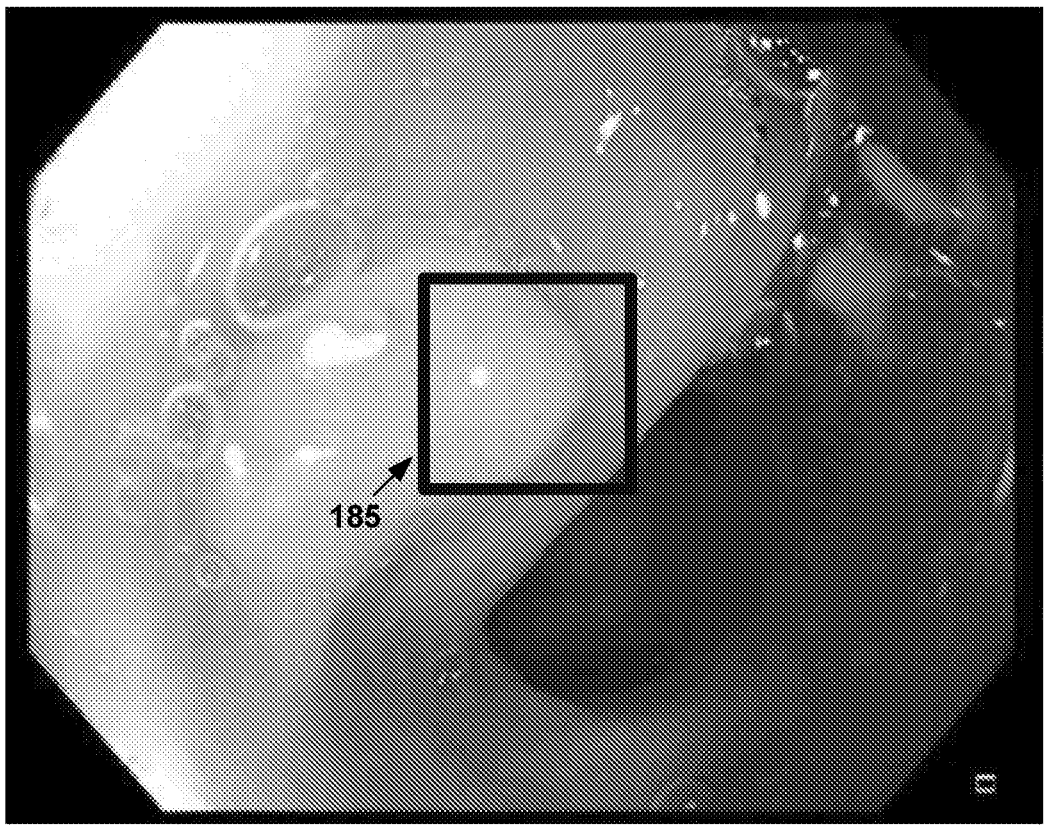
FIG. 1C is an illustrative example of an interface that includes a bounding box around an area of a colonoscopic image that likely includes a polyp, where the bounding box can be presented in instances in which a probability that the image includes a polyp is greater than a threshold probability (e.g., a probability of greater than 50% of being a polyp) in accordance with some embodiments of the disclosed subject matter.

In response to determining that the probability that a polyp is present in an informative image frame at 150 (e.g., the polyp probability being greater than a polyp classification threshold), process 100 can proceed to step 160, where an alert or notification of the presence of the detected polyp can be presented. For example, as shown in FIG. 1C, in response to determining that the probability that an informative frame 180 contains a polyp is greater than a predetermined probabilistic threshold, the informative image frame 180 can be presented along with a bounding box 185 or other indication showing a region of interest containing the detected polyp within the informative image frame. In a more particular example, bounding box 185 can be presented around a detected polyp to an operator in response to the determined probability being greater than a particular classification threshold value, where the classification threshold value can be configured by the operator of the polyp detection system (e.g., place a bounding box when the probability that an image frame includes a polyp is greater than 60%).

It should be noted that, in some embodiments, informative image frame 180 with the detected polyp in region 185 can be presented with any other suitable information to assist the user performing the procedure, such as the informativeness score for image frame 180, a polyp probability score determined using one or more machine learning techniques, polyp location information, image frame information, video information, polyp shape information, polyp size information, polyp color information, polyp property information, etc. It should also be noted that the type of information presented along with informative image frame 180 and bounding box 185 can be configured by the operator of the polyp detection system.

This can, for example, direct the attention of the endoscopist towards a detected polyp, thus increasing endoscopist attentiveness and reducing polyp miss rates.

Referring back to FIG. 1A, in response to not detecting a polyp (a non-polyp classification) at 150, process 100 can return to 110 and wait to receive additional image frames from an optical colonoscopic video. Alternatively, process 100 can return to 140 and wait to receive additional informative image frames.

In some embodiments, the quality monitor can be implemented using any suitable machine learning technique to determine whether one or more image frames in a colonoscopic video (or any other suitable image dataset) includes informative images or non-informative images.

Figure 2:
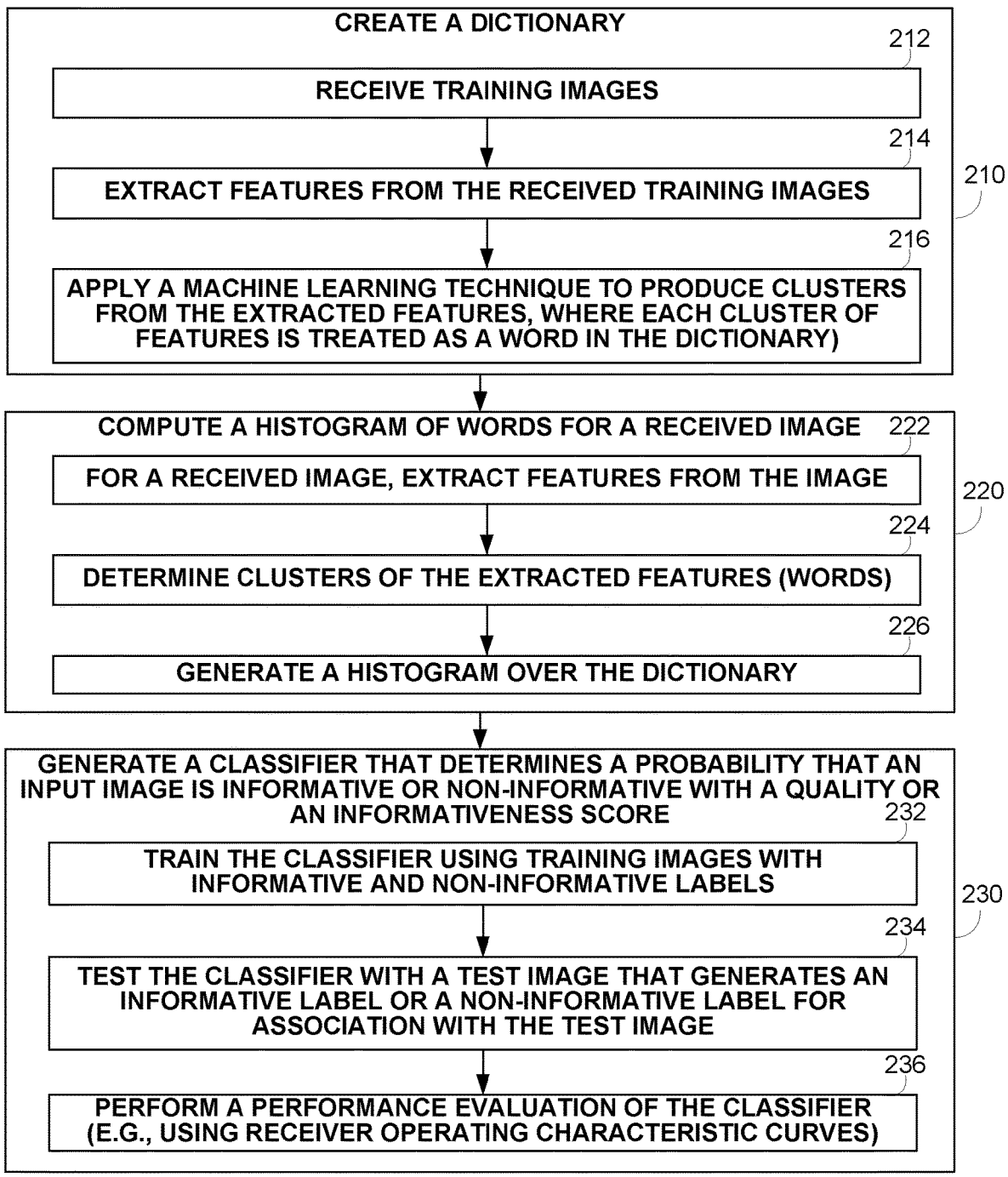
FIG. 2 is an illustrative example of a process for implementing a quality monitor including a classifier that can determine a probability that an image is informative or non-informative in accordance with some embodiments of the disclosed subject matter.

FIG. 2 is an illustrative example of a process for implementing a quality monitor including a bag of visual words classifier to differentiate between informative images and non-informative images in accordance with some embodiments of the disclosed subject matter. It should be noted that the bag of visual words classifier can be used as informative images and non-informative images can generally consist of inherently different patterns in their makeup. As described above, non-informative image frames are generally blurry and nearly uniform in approach with few areas of potentially useful information, while informative image frames generally include crisp edges and varying levels of dark and light regions with useful information spread throughout the image frame.

Turning to FIG. 2, process 200 can begin by creating a dictionary of visual words for the bag of visual words classifier from training images at 210. This can include receiving training images at 212, extracting features from the received training images at 214, and applying a machine learning technique to produce clusters of features at 216.

Figure 3:
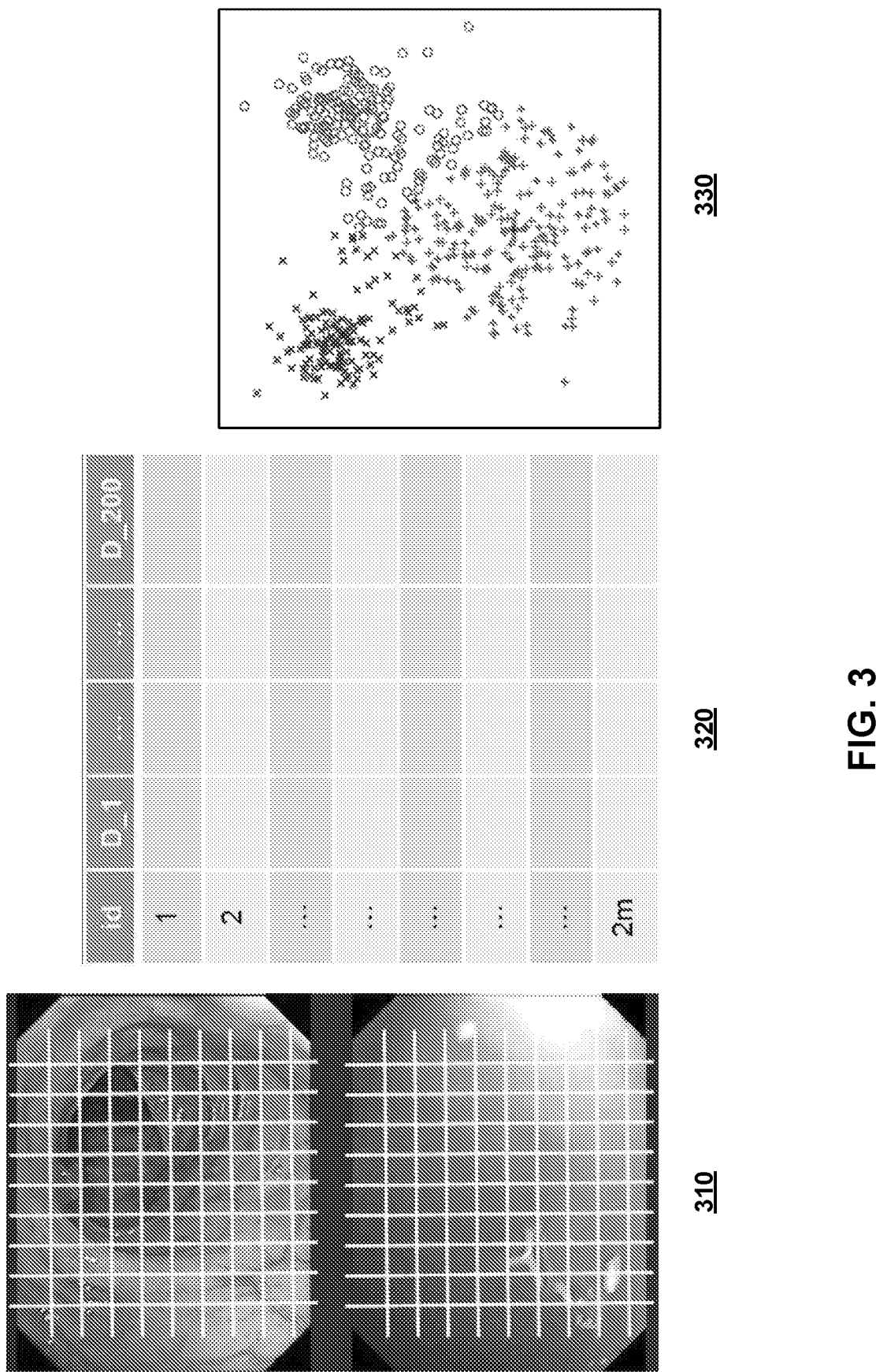
FIG. 3 is an illustrative example of a cluster of words in a dictionary that is derived from features extracted from training images in accordance with some embodiments of the disclosed subject matter.

For example, in response to receiving a set of training images at 210, multiple points within each of the training images can be selected. Such points can be selected from each training image by random sampling, key point detection, spatial pyramid, or any other suitable technique. An image descriptor can then be used to extract features from the received training images at 214. In a more particular example, a DAISY image descriptor can be used that stores local gradient information around each pixel via orientation maps convolved with Gaussian filters. In response, a vector of features can be found at each pixel. For example, upon selecting five hundred random points from each of two thousand training images, DAISY features can be computed from each of the training images—i.e., those features found at five hundred points in each of the two thousand training images. In continuing this example, the extracted DAISY features can be clustered using a k-means clustering approach, where the centroids of these clusters represent the visual words of the bag of visual words classifier. An example of this is shown in FIG. 3, where training images are sampled at 310, features are extracted using the image descriptor at 320, and clusters of features were generated at 330, where each cluster can represent a visual word in the dictionary of visual words.

It should be noted that process 200 can repeat the dictionary creation at 210 and, in particular, the clustering approach at 216, any suitable number of times. For example, the application of the k-means clustering approach with different numbers of clusters can be used to change the size of the dictionary of visual words.

It should also be noted that, in some embodiments, any other suitable image descriptors can be used, such as a rotation invariant DAISY (O-DAISY) image descriptor or a Scale Invariant Feature Transform (SIFT) image descriptor. For example, the implemented DAISY image descriptor can be adjusted to become rotation invariant for extracting features by computing the gradient orientation at each pixel and rotating the descriptor relative to the gradient orientation.

Referring back to FIG. 3, at 220, a histogram of words can be generated for an image. This can include extracting features from a received training image at 222, determining the words from the dictionary of visual words or clusters associated with the extracted features at 224, and generating a histogram of words over the dictionary of visual words at 226. Extracted features can be converted into histograms for each image using visual words such that the bins can represents the visual words and the value associated with each bin can indicate the number of features belonging to that word.

Figure 4:
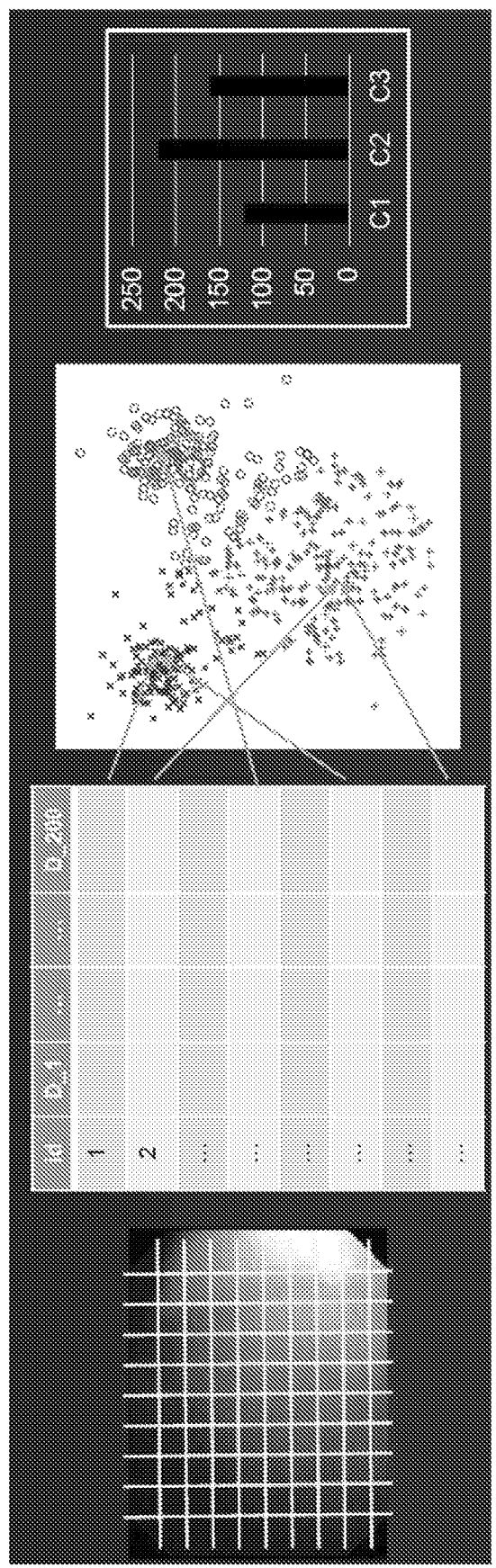
FIG. 4 is an illustrative example of a process for generating a histogram of words from the clusters or words associated with an image in accordance with some embodiments of the disclosed subject matter.

For example, as shown in FIG. 4, points within each of the training images can be selected from each of the training images by re-sampling random points 410 and DAISY features can be extracted at 420. Words or clusters can be determined from the extracted features at 430 and a histogram of the clusters (C1, C2, C3, etc.) can be generated at 440.

It should be noted that, in some embodiments, the generated histogram, such as histogram 440 in FIG. 4, can be normalized based on the number of sampled points used in its formation.

Referring back to FIG. 3, a classifier can be generated that determines a probability that an input image is informative or non-informative at 230. For example, a random forest (RF) model can be generated for classifying images as being informative or non-informative.

Figure 5A:
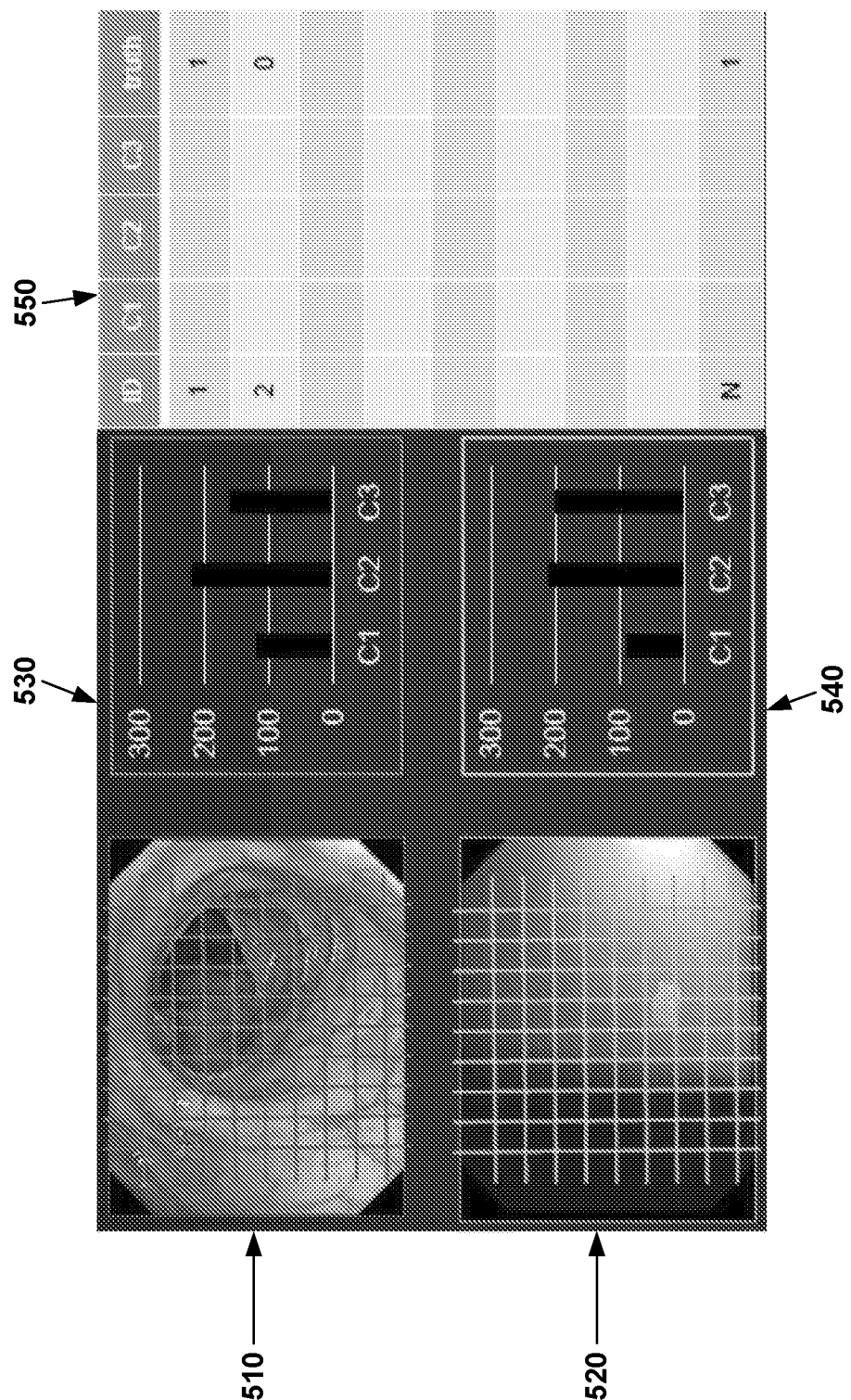
FIG. 5A is an illustrative example of a process for training a classifier that can determine a probability that an image is informative or non-informative, where the classifier is trained with training images each having an assigned informative label or non-informative label, in accordance with some embodiments of the disclosed subject matter.

In some embodiments, the random forest classifier can be trained using training images with informative and non-informative labels at 232. For example, as shown in FIG. 5A, the random forest classifier can be trained using training images that include informative images, such as informative image 510, and non-informative images, such as non-informative image 520. Each of these training images can have an associated histogram, such as histogram 530 that is associated with image 510 and histogram 540 that is associated with image 520. It should be noted that, because a histogram is formed for each training image from a set of training images, these histograms along with corresponding ground truth labels of informativeness shown in 550 (e.g., an informative label, a non-informative label, an informativeness score, etc.) can be used to construct the random forest model.

It should be noted that the random forest classifier can be trained to classify an image based on the number of features belonging to each visual word in that image, which can be expected to differ between informative and non-informative image frames based on the different patterns present in these images as described above.

Referring back to FIG. 3, the random forest classifier can be tested with a test image that generates an informative label or a non-informative label for association with the test image at 234. For example, in response to receiving a test image, a random sampling of points can be selected from the test image and DAISY features can be extracted on each of these points, which can then be converted into a histogram based on the visual words that were identified during the training at 232. The test image can then be classified as informative or non-informative based on its histogram using the random forest model.

It should be noted that, upon receiving an image dataset having ground truth labels for training and testing the random forest classifier, any suitable approach can be used to divide the image dataset. For example, a randomly selected half of the image dataset can be used for training the random forest classifier and the remaining half of the image data can be used to test the random forest classifier.

Figure 5B:
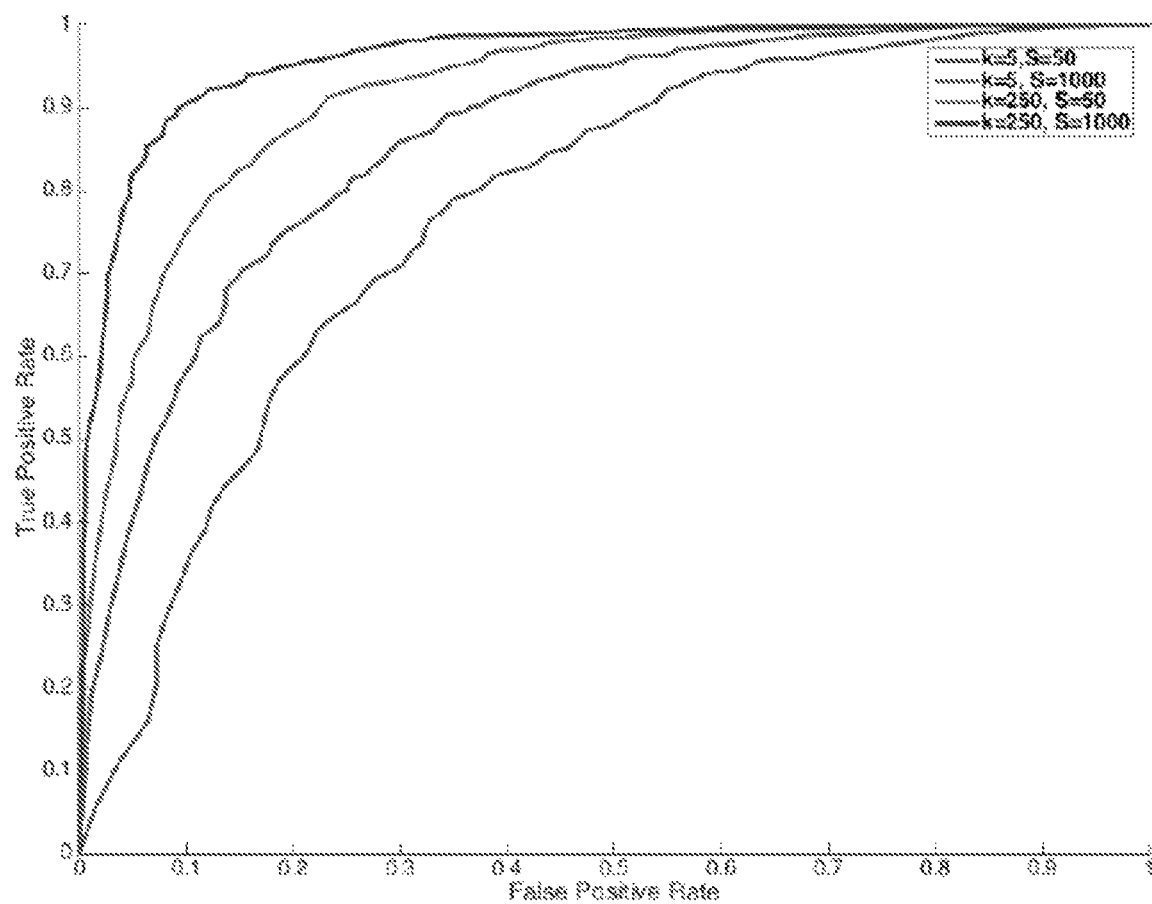
FIG. 5B is an illustrative example of receiver operating characteristic curves for the random forest classifier and associated area under the receiver operating characteristic curve measurements in accordance with some embodiments of the disclosed subject matter.

In some embodiments, the quality monitor can evaluate the performance of the random forest classifier. For example, based on the predicted output from the random forest model and the ground truth of the testing images, the performance of the random forest classifier can be evaluated by reviewing the area under the receiver operating characteristic (ROC) curve. The area under the receiver operating characteristic curve measurements can be used to determine performance of the random forest classifier using a different number of clusters (words) and/or a different number of sampled points. An illustrative example of receiver operating characteristic curves and the associated area under receiver operating characteristic curve measurements is shown in FIG. 5B. Accordingly, the number of clusters and the number of sampled points for constructing the random forest classifier in a bag of visual words approach can be selected based on the receiver operating characteristic curves and the associated area under receiver operating characteristic curve measurements is shown in FIG. 5B.

Figure 6:
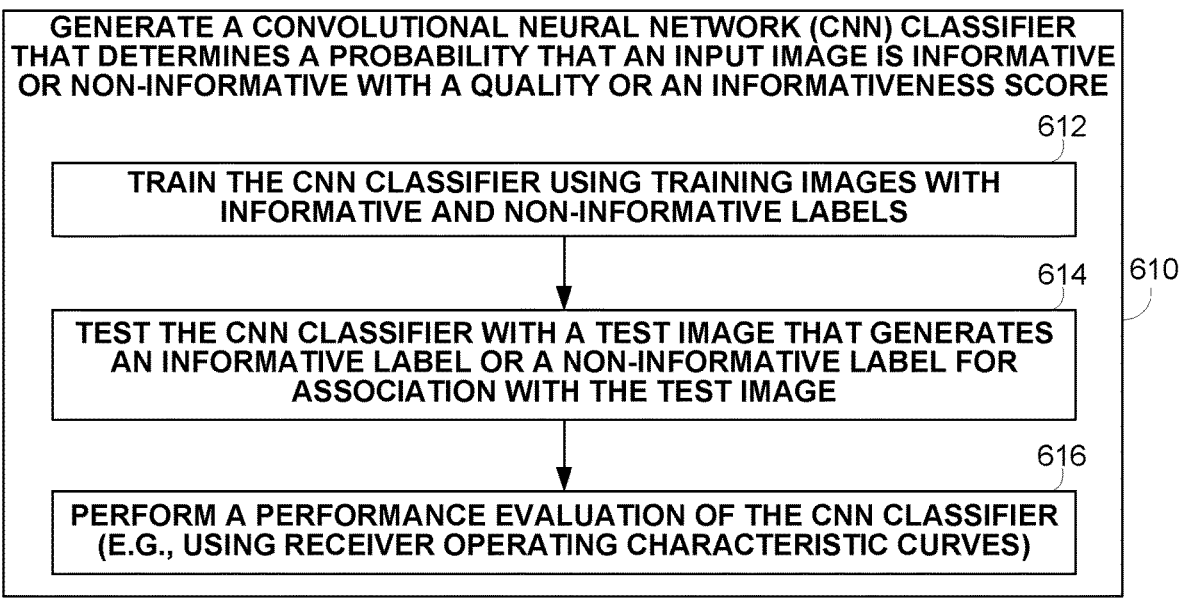
FIG. 6 is an illustrative example of a process for implementing a quality monitor including a convolutional neural network classifier that determines a probability that an image is informative or non-informative in accordance with some embodiments of the disclosed subject matter.

Additionally or alternatively, the quality monitor can be implemented using a convolutional neural network classifier to classify images as being informative images or non-informative images. FIG. 6 shows an illustrative example of a process 600 for implementing a quality monitor including a convolutional neural network classifier that determines a probability that an image is informative or non-informative in accordance with some embodiments of the disclosed subject matter. Generally speaking, instead of performing feature extraction as in the random forest classifier, the images are passed to the convolutional neural network classifier, thereby allowing the convolutional neural network classifier to identify the features. It should be noted that the convolutional neural network classifier generates features through an iterative process of convolving images with filters followed by subsampling. The convolution can result in feature maps of salient features, such as edges and lines, while the subsampling can serve to reduce image resolution and size through averaging. In turn, final features maps can be obtained and sent to the classification layer of the convolutional neural network classifier in the form of vectors.

As shown in FIG. 6, process 600 can begin by training the convolutional neural network classifier using training images that each have an informative or non-informative label. As described above, upon receiving an image dataset having ground truth labels for training and testing the convolutional neural network classifier, any suitable approach can be used to divide the image dataset. For example, a randomly selected half of the image dataset can be used for training the convolutional neural network classifier and the remaining half of the image data can be used to test the convolutional neural network classifier.

Figure 7:
FIG. 7 is an illustrative example of training images, where each training image has an assigned label (e.g., Y=0 for informative or Y=1 for non-informative) in accordance with some embodiments of the disclosed subject matter.
Figure 7:
Figure 7:
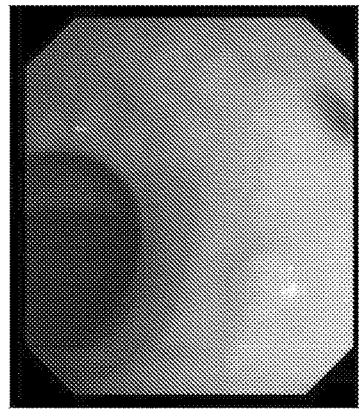
Figure 8:
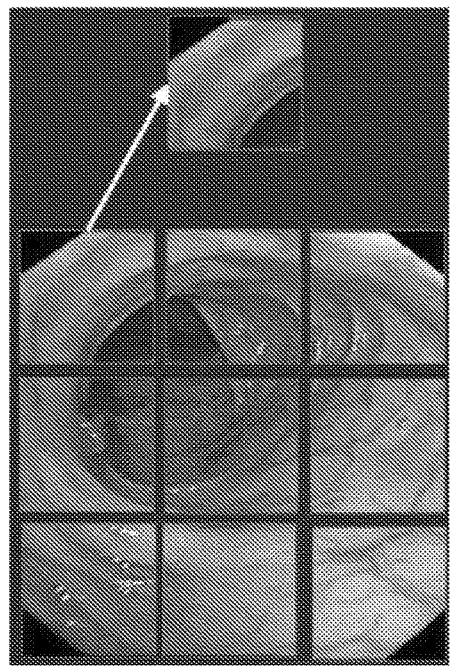
FIG. 8 is an illustrative example showing that a training image can be divided into multiple patches (e.g., nine patches) in accordance with some embodiments of the disclosed subject matter.
Figure 8:
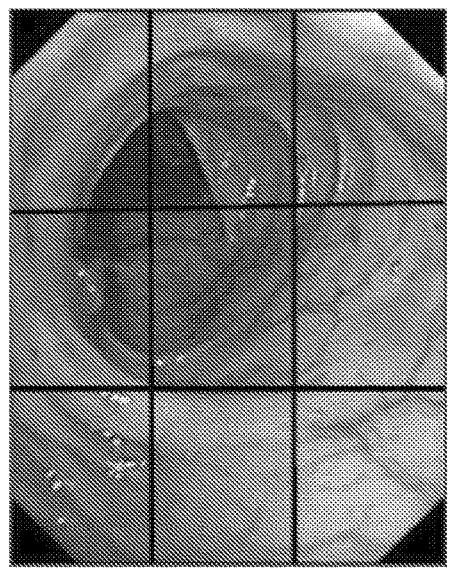
Figure 9:
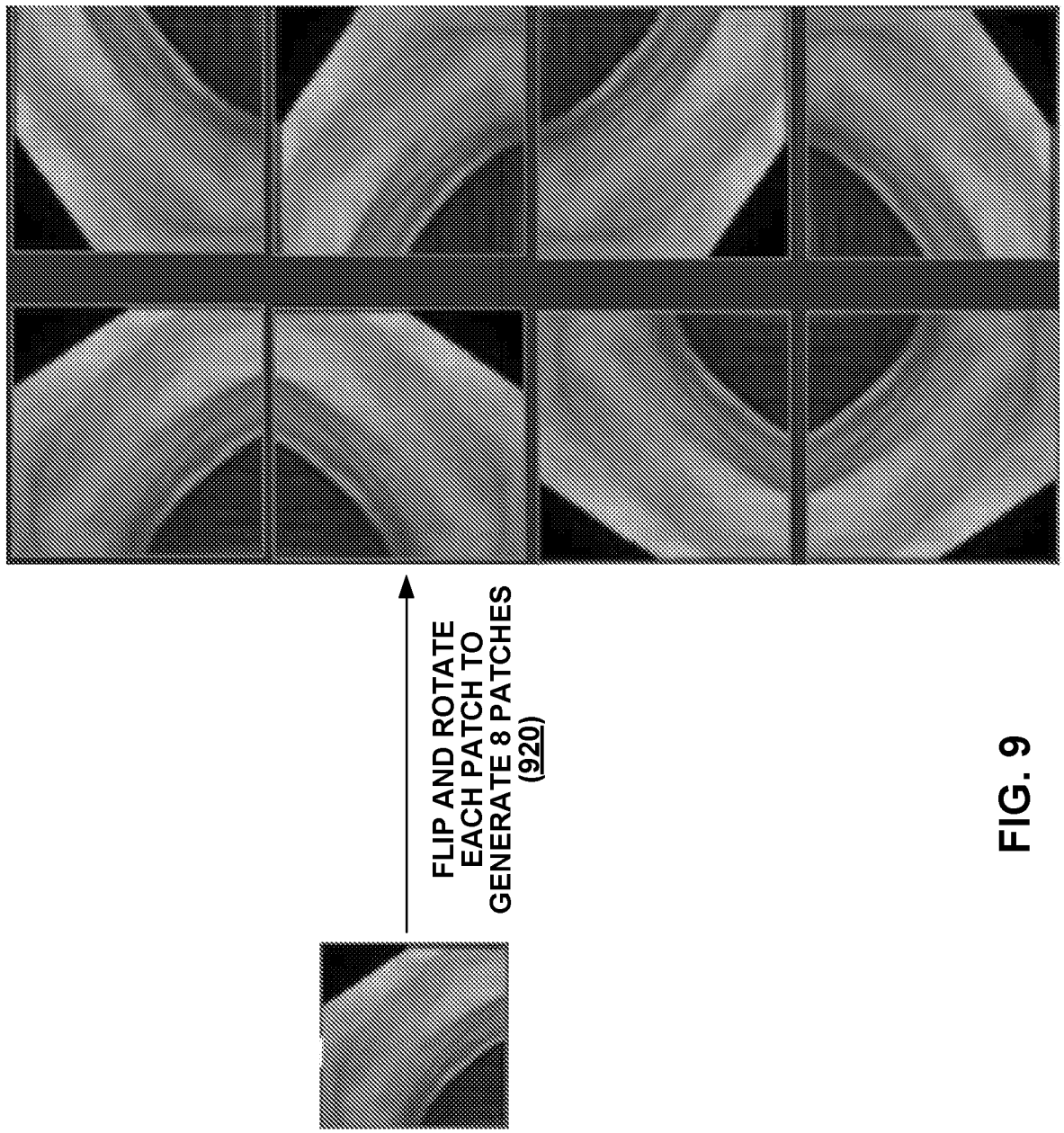
FIG. 9 is an illustrative example showing multiple patches that are generated from a divided patch in a training image in accordance with some embodiments of the disclosed subject matter.
Figure 10:
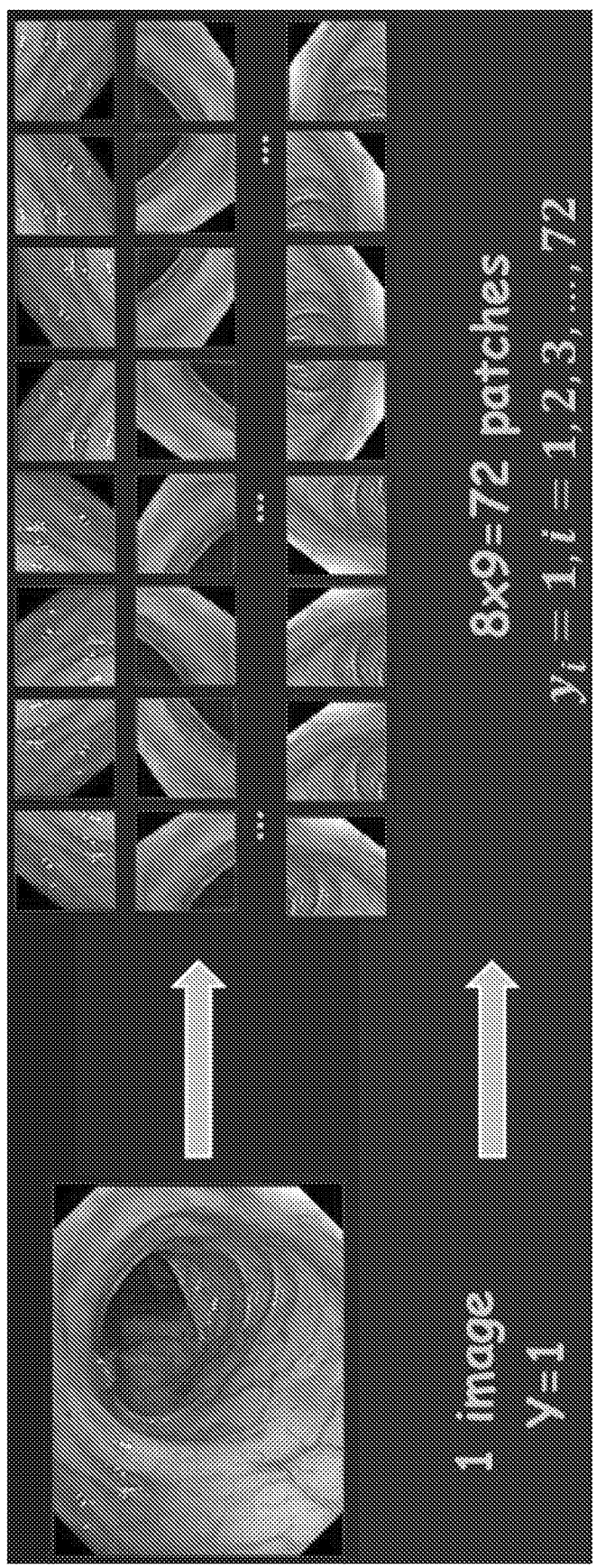
FIG. 10 is an illustrative example showing multiple patches that are generated from the divided patches in a training image (e.g., seventy-two patches from a single training image) and the labels associated with each of the patches in accordance with some embodiments of the disclosed subject matter.

In some embodiments, training patches can be generated from each training image. As shown in FIG. 7, training images, such as training images 710, 720, and 730, can each have associated labels—e.g., y=0 for non-informative images having minimal information content and y=1 for informative images having maximum information content. As shown in FIG. 8, each training image can be divided into any suitable number of N patches. For example, in FIG. 8, training image 710 has been divided into nine training patches. As shown in FIG. 9, each patch can be flipped and/or rotated to generate eight training patches from each original patch. For example, in FIG. 9, eight versions of a patch that was divided from training image 710 can be generated by rotating the original patch clockwise by 90 degrees, 180 degrees, and 270 degrees, followed by generating the mirror image of each of these patches including the original patch.

Accordingly, each training image having an informativeness label can be used to obtain seventy-two training patches with the same informativeness label. For example, for an informative training image 710 with y=1, each of the seventy-two training patches having the same label ($y_i$=1, i=1, 2, 3, . . . , 72). This can, for example, increase the dataset of training images used to train the convolutional neural network classifier.

It should be noted that, in some embodiments, the obtained training patches can be resized to a particular size (e.g., 28×28, 32×32, etc.).

The convolutional neural network classifier can then be trained using the obtained training patches. It should be noted that the convolutional neural network classifier can be composed of multiple layers having any suitable number of convolution steps and any suitable number of subsampling steps.

In a more particular example, the convolutional neural network classifier can include four layers including two convolution steps and two subsampling steps. The first layer can convolve the original images with six filters of size 5×5, followed by subsampling the resulting images to reduce their size by half. Treating the resulting images as its input, the third layer of the convolutional neural network classifier can convolve these images with twelve filters of size 5×5, followed by again subsampling the resulting images to reduce their size by half.

In some embodiments, in addition to the network architecture, other input parameters to the convolutional neural network classifier can include alpha, batch size, and the number of epochs. Generally speaking, alpha can be used to define the learning rate of the convolutional neural network classifier, batch size can specify the number of images to be used in each iteration, and the number of epochs can denote the number of full passes to perform through the entire dataset.

Referring back to FIG. 6, process 600 can continue by testing the convolutional neural network classifier with a test image that generates an informative label or a non-informative label for association with the test image. This is described further in connection with FIG. 11.

Figure 11:
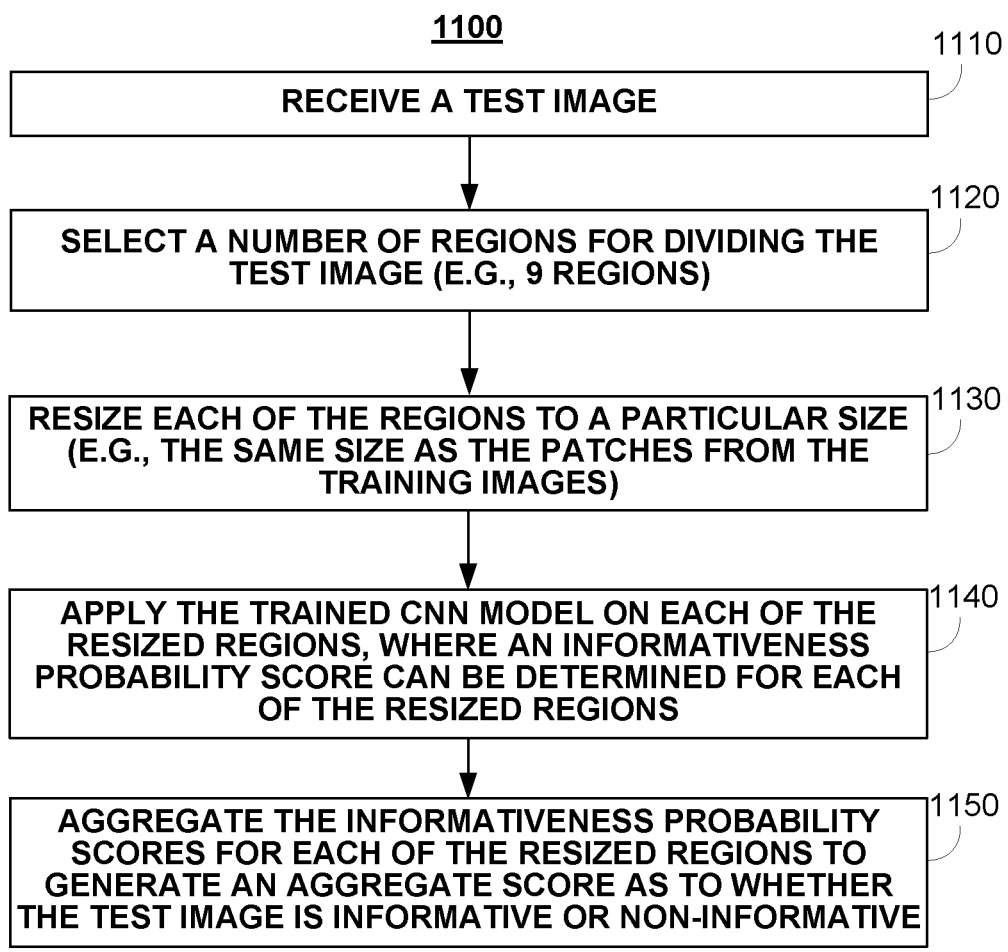
FIG. 11 is an illustrative example of a process for testing the convolutional neural network classifier described in FIG. 6 that determines a probability that an image is informative or non-informative in accordance with some embodiments of the disclosed subject matter.

Turning to FIG. 11, process 1100 can begin by receiving a test image at 1110. As described above, a remaining subset of images divided from the image dataset can be used to test the convolutional neural network classifier.

For each test image, a number of regions can be selected to divide the test image at 1120. For example, similar to the generation of training patches described above, a test image can be divided into nine regions. At 1130, each of the selected regions divided from the test image can be resized. For example, the selected regions divided from the test image can be resized such that each selected region is the same size as the training patches obtained from the training images (e.g., 28×28, 32×32, etc.).

At 1140, the trained convolutional neural network classifier can be applied to each of the selected and resized regions, where an informativeness probability score can be determined for each of the regions. At 1150, the informativeness probability scores for each of the resized regions can be aggregated to generate an aggregate probability score. This aggregated probability score can, for example, be used to determine whether the test image is associated with an informative label or a non-informative label. For example, in response to the aggregate probability score for the test image being greater than 51%, the test image can be associated with a label indicating that the test image includes informative content.

It should be noted that, in some embodiments, classification thresholds, such as the aggregate probability score needed to be deemed an informative image, can be set by an operator of the quality monitor system.

In some embodiments, as described above, the quality monitor can evaluate the performance of the convolutional neural network classifier. For example, based on the aggregate probabilistic output from the convolutional neural network classifier and the ground truth of the testing images, the performance of the convolutional neural network classifier can be evaluated by reviewing the area under the receiver operating characteristic (ROC) curve. The area under the receiver operating characteristic curve measurements can be used to determine performance of the convolutional neural network classifier using different batch sizes and/or different numbers of epochs. Accordingly, the batch size and/or the number of epochs for constructing the convolutional neural network classifier can be selected based on the receiver operating characteristic curves and the associated area under receiver operating characteristic curve measurements.

In some embodiments, the quality monitor can use the performance evaluation data to select between machine learning classifiers. For example, in some embodiments, the quality monitor can use the performance evaluation data to select between using a random forest classifier and a convolutional neural network classifier on a colonoscopic video having multiple image frames.

In some embodiments, the informativeness labels (or scores) can be used in any suitable number of applications. For example, an operator of an optical colonoscopy system can receive an indication as to the informativeness of the images as the procedure is being performed. In this example, an indication of one or more non-informative images can alert the operator of the onset of a hasty or poor examination and encourage a more diligent procedure. In addition, the indication of one or more non-informative images can alert the operator that the past segment of the colon should be re-examined. In another example, an operator of an optical colonoscopy system can receive an indication as to the informativeness of the images as the procedure is being performed, while image frames from the optical colonoscopic system that are deemed to be informative (e.g., have an informativeness score greater than a particular classification threshold) can be automatically transmitted to a polyp detection system for further analysis.

In accordance with some embodiments of the disclosed subject matter, upon determining which image frames from the colonoscopic video are deemed informative (e.g., having an informativeness score or any other suitable probability greater than a threshold value), these image frames can be transmitted to a polyp detection system for simultaneously determining the likelihood that a polyp is present in an informative image frame. Such a polyp detection system can be implemented using any suitable machine learning technique and any suitable number of machine learning techniques to determine whether one or more informative image frames contains a polyp or a polyp-like object.

In a more particular example, to implement a polyp detection system that can automatically detect polyps or polyp-like objects in images of a colonoscopic video, the polyp detection system can identify polyp edges by extracting features from pixels and passing these features to a random forest classification model for distinguishing between polyp edges and non-polyp edges. Based on the result of this classification from the random forest classifier, the polyp detection system can then detect polyps by applying a Hough transform on refined edge maps reconstructed from the random forest classifications. The detected circles from the Hough transform can serve as the basis for constructing image patches from each image, which can then be passed to a convolutional neural network classifier for classifying image patches as containing a polyp or a non-polyp.

Figure 12:
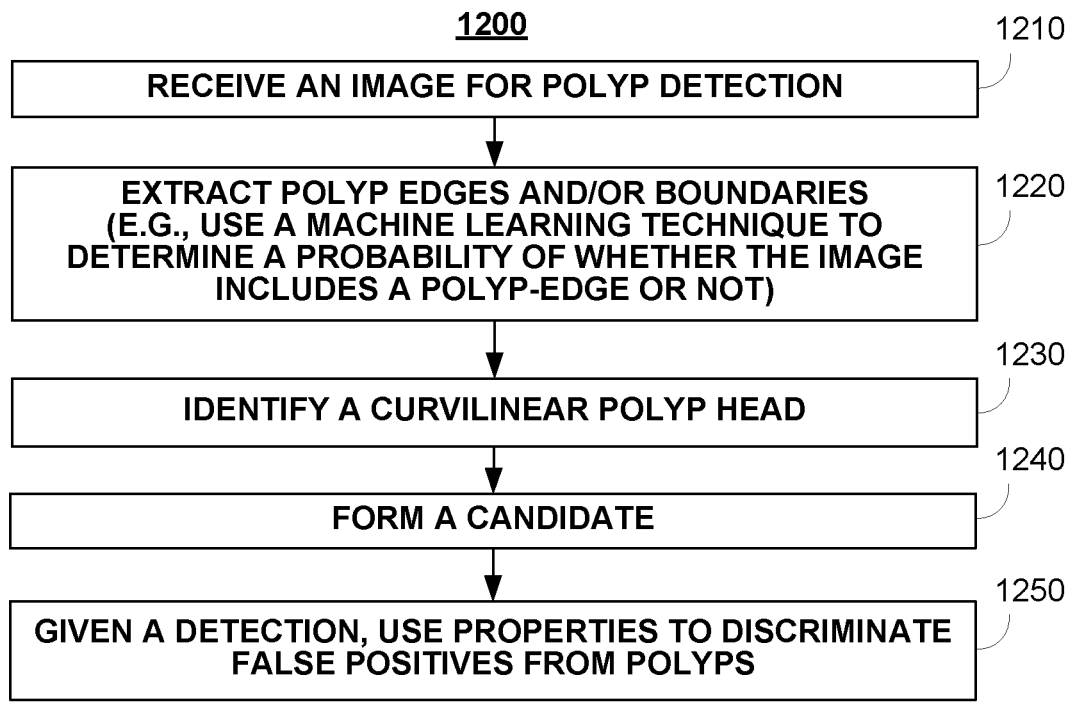
FIG. 12 is an illustrative example of a process for implementing a polyp detector that uses polyp properties to discriminate false positives from polyps in accordance with some embodiments of the disclosed subject matter.

FIG. 12 is an illustrative example of a process for implementing a polyp detector that uses polyp properties to discriminate false positives from polyps in accordance with some embodiments of the disclosed subject matter. As shown in FIG. 12, an image, such as an informative image from the quality monitor system, can be received at 1210. At 1220, in response to receiving an image for polyp detection, polyp edges and/or boundaries can be determined from the image using a machine learning technique that determines a probability of whether the image includes a polyp edge or a non-polyp edge. This can, for example, filter or reduce the relevant search space for finding polyp within the image by localizing those pixels of the image that are likely to encompass polyp edges.

At 1230, upon classifying the pixels as likely to contain a polyp edge or not, the polyp detector can determine whether at least one curvilinear head is present at these extracted boundaries. Based on this information, polyp candidates can be formed at 1240 and a convolutional neural network classifier can be used to determine whether a polyp candidate includes a polyp or not at 1250. In particular, the convolutional neural network classifier can use polyp properties associated with the polyp candidate to determine a probability that the polyp candidate contains a true polyp while sustaining a low false positive rate.

Referring back to 1220, the polyp detector can classify whether pixels in a received image include a polyp edge or a non-polyp edge. This edge detection can be performed using any suitable approach. For example, as shown in the illustrative process of FIG. 13, polyp edges and/or boundaries can be extracted using a random forest classifier. In another example, as shown in the illustrative process of FIG. 16, polyp edges and/or boundaries can be extracted using a convolutional neural network classifier. It should be noted that colonoscopy images contain other edges aside from those surrounding polyps, such as ridges or curves along the colon wall. As such, traditional edge detection techniques may capture too many edges, thereby worsening the Hough transform result.

Figure 13:
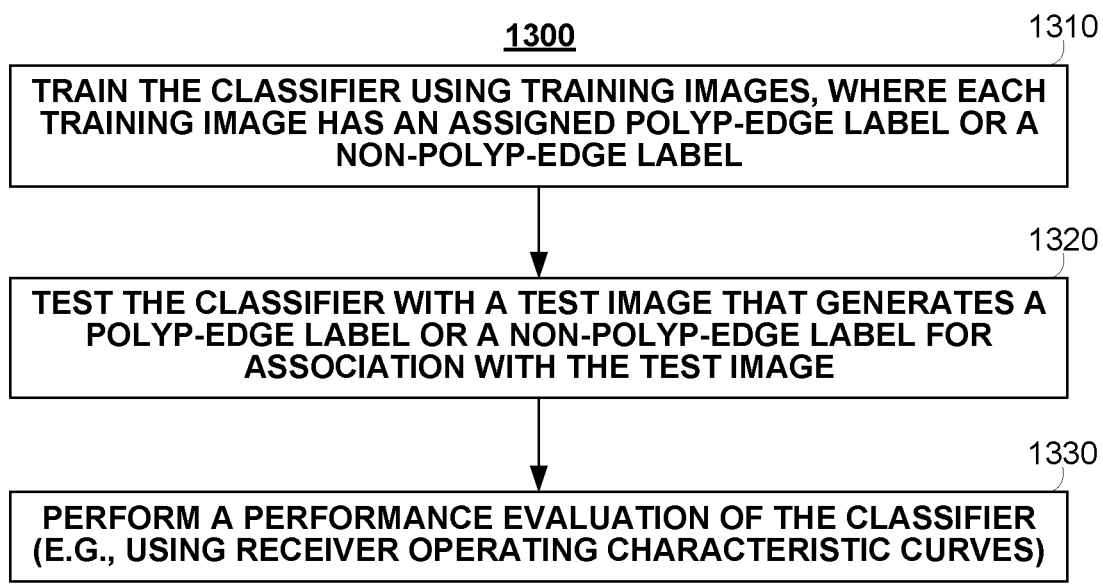
FIG. 13 is an illustrative example of a process for extracting polyp edges and/or boundaries using a classifier, such as a random forest classifier, in accordance with some embodiments of the disclosed subject matter.

Turning to FIG. 13, FIG. 13 is an illustrative example of a process 1300 for extracting polyp edges and/or boundaries using a classifier, such as a random forest classifier, in accordance with some embodiments of the disclosed subject matter.

Process 1300 begins by training the random forest classifier using training images in which each of the training images is associated with a polyp edge label or a non-polyp edge label. For example, a set of training images can be obtained, where the set of training images includes positive samples that correspond to pixels having a true polyp edge and negative samples that correspond to pixels that are not part of a polyp edge. It should be noted that, in addition to a label indicating whether a training image has a polyp edge or not, the training image can be associated with a classification score of the probability that the training image includes a polyp edge.

It should be noted that any suitable approach can be used to obtain positive and negative samples from the training images. For example, a set of edge pixels can be generated using any suitable edge detector.

In some embodiments, a Canny edge detector with sampling can be used to obtain positive and negative samples from the training images. This can apply the Canny edge detector to each training image to obtain an edge map. The corresponding ground truth image can then be dilated with a 7×7 structure element composed of ones, which served to increase the band of pixels identified as belonging to the polyp edge. For the positive samples, pixels that are common to both the Canny edge map and the dilated ground truth image can be selected as positive samples corresponding to pixels having a true polyp edge. Additionally, a given number of points can be randomly sampled from the edge pixels. For example, a maximum of 200 points can be randomly sampled from the image. For the negative samples, the pixels that matched between the Canny edge map and the dilated ground truth image from the original Canny edge map can be removed, which can generate an edge map that excludes the polyp. From the remaining edge pixels, a number of negative pixels can be randomly sampled. It should be noted that the number of negative samples can be the same as the number of positive samples selected above.

Alternatively, in some embodiments, a Canny edge detector without any sampling can be used to obtain positive and negative samples from the training images. As described above, this approach can apply the Canny edge detector to each training image to obtain an edge map for the training image. The corresponding ground truth image can then be dilated with a 7×7 structure element composed of ones, which served to increase the band of pixels identified as belonging to the polyp edge. For the positive samples, all of the pixels that are common to both the Canny edge map and the dilated ground truth image can be selected. For the negative samples, all of the remaining edge pixels after removing the polyp edges from the Canny edge map can be selected.

Alternatively, in some embodiments, a Canny edge detector may not be used to generate a Canny edge map. The ground truth image for each training image can be dilated using a 7×7 structuring element composed of ones, which served to increase the band of pixels identified as belonging to the polyp edge. In this approach, all of the pixels from this ground truth image can be used as the positive samples. For the negative samples, the ground truth pixels can be removed from the original image and, from the remaining points, pixels can be randomly sampled in order to obtain the same number of negative and positive samples for each training images. These negative samples can, for example, be composed of both edge and non-edge pixels.

Figure 14:
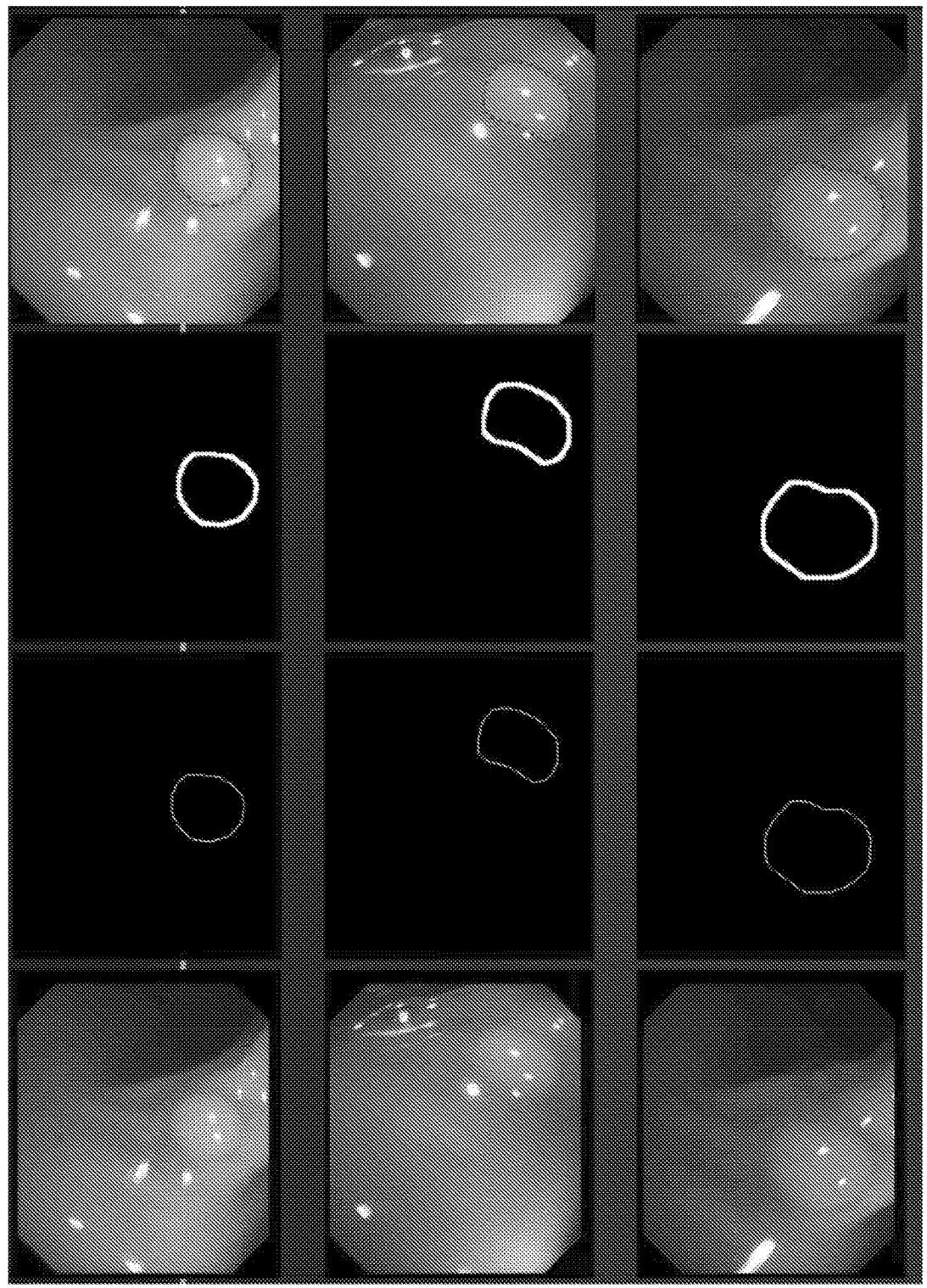
FIGS. 14 and 15 are illustrative examples of extracting polyp edges from an image in accordance with some embodiments of the disclosed subject matter.

FIG. 14 shows illustrative examples of an original image, which is followed by a ground truth image, which is followed by a dilated ground truth image (e.g., in the approach using the Canny edge detector), and which is followed by an original image without the ground truth image (e.g., in the approach without using the Canny edge detector).

Upon obtaining positive and negative samples from the training images, features can be extracted at each of these pixels. For example, after finding positive and negative points for each image using one of the above-mentioned approaches (e.g., Canny edge detection with sampling, Canny edge detection without sampling, etc.), features can be extracted at the corresponding pixel locations of these sampled points in the original training images. Similar to the feature extraction described above, the DAISY image descriptor can be used to extract features, which uses orientation maps convolved with Gaussian filters for computing gradient information in a small neighborhood of points surrounding each pixel.

It should be noted that any suitable image descriptor can be used to extract features from the training images. It should also be noted, however, that an image descriptor, such as the DAISY image descriptor, can be selected for feature extraction in polyp detection given that polyps can appear in any number of orientations in an image. It should further be noted that, in some embodiments, the DAISY image descriptor can be modified to become rotation invariant for extracting features by computing the gradient orientation at each pixel and rotating the descriptor relative to the gradient orientation.

Figure 15:
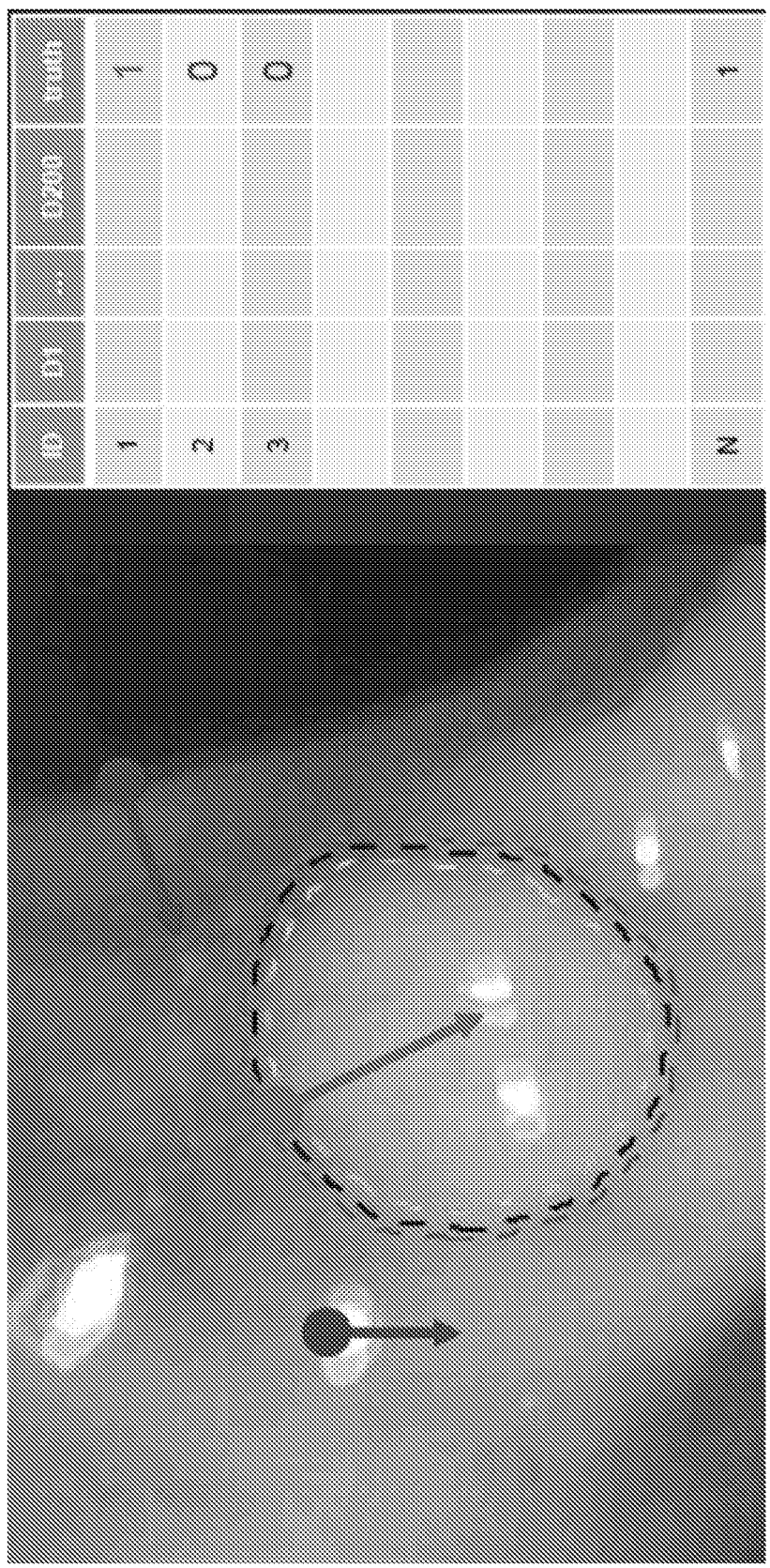

Upon extracting features from the training images, a random forest classifier can be constructed using these features and the corresponding ground truth of each pixel. The random forest classifier can be used to classify pixels as containing a polyp edge or a non-polyp edge. For example, the computed DAISY image descriptor features from each of the training images along with the ground truth for each corresponding pixel can be provided to the random forest classifier for training the classifier (e.g., 100 trees for all random forest models). An illustrative example of a table including the computed DAISY image descriptor features from an image along with the ground truth for each corresponding pixel is shown in FIG. 15. Such a table can be transmitted to the random forest classifier for training.

Referring back to FIG. 13, process 1300 can continue at 1320 by testing the random forest classifier with a test image, where the random forest classifier can generate a polyp edge label or a non-polyp edge label for association with the test image.

For example, when using a Canny edge detector to obtain a Canny edge map of a testing image, the Canny edge detector can be applied to find all of the edges in a test image. DAISY image descriptor features can then be computed at all of these edge pixel locations in the test image, which can be sent to the trained random forest classifier. The trained random forest classifier can classify each pixel as a polyp edge or a non-polyp edge.

In another example, when not using a Canny edge detector to obtain a Canny edge map of a testing image, DAISY image descriptor features can be computed at all of the pixels in the testing image, which can then be sent to the trained random forest classifier. The trained random forest classifier can classify each pixel as a polyp edge or a no-polyp edge.

In some embodiments, at 1330, process 1300 can cause the polyp detector to perform a performance evaluation of the random forest classifier. For example, based on the predicted output from the random forest model and the ground truth of the pixels of the testing images, the performance of the random forest classifier can be evaluated by reviewing the area under the receiver operating characteristic (ROC) curve. The area under the receiver operating characteristic curve measurements can be used to determine performance of the random forest classifier using a different edge detection approaches. For example, the edge detection approach, such as edge detection without the Canny edge detector or random sampling, can be selected based on the receiver operating characteristic curves and the associated area under receiver operating characteristic curve measurements.

Figure 16:
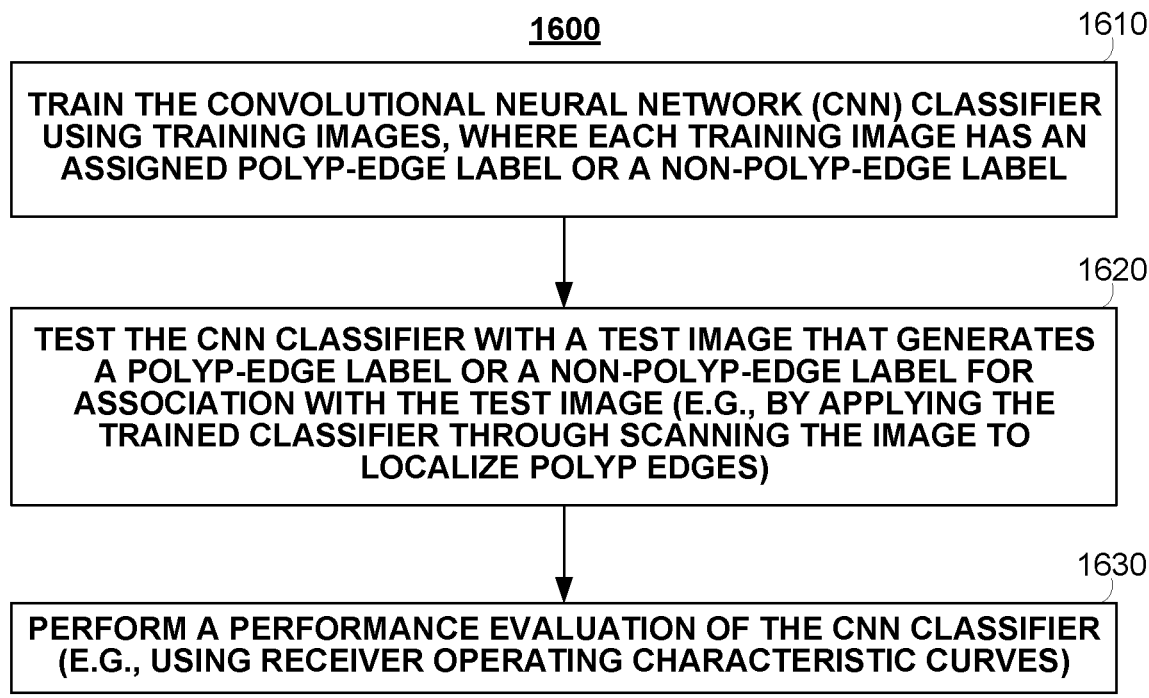
FIG. 16 is an illustrative example of a process for extracting polyp edges and/or boundaries using a convolutional neural network classifier, where the classifier localizes polyp edges and generates a polyp edge label or a non-polyp edge label, in accordance with some embodiments of the disclosed subject matter.

Additionally or alternatively to using a random forest classifier, FIG. 16 shows an illustrative example of a process 1600 for extracting polyp edges and/or boundaries using a classifier, such as a convolutional neural network classifier, in accordance with some embodiments of the disclosed subject matter.

Figure 17:
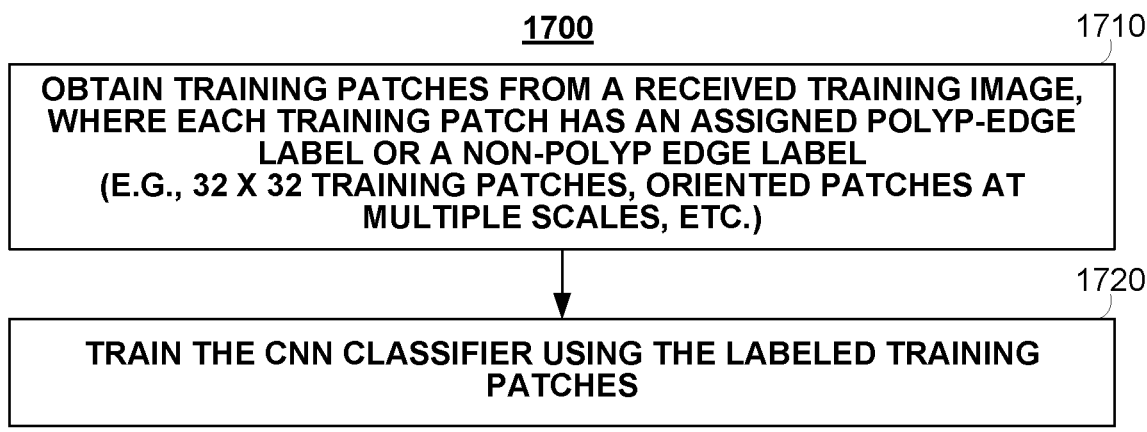
FIG. 17 is an illustrative example of a process for training the convolutional neural network classifier described in FIG. 16 in accordance with some embodiments of the disclosed subject matter.

As shown, process 1600 can begin by training the convolutional neural network classifier using training images in which each training image is assigned a polyp edge label or a non-polyp edge label. For example, FIG. 17 shows an illustrative example of a process 1700 for training the convolutional neural network classifier described in FIG. 16 in accordance with some embodiments of the disclosed subject matter. Process 1700 can begin by receiving training images, where each training image has an assigned polyp edge label or a non-polyp edge label. For example, as described above, various approaches can be used to obtain a set of training images and then divide the set of training images into a subset of positive samples that correspond to pixels having a true polyp edge and negative samples that correspond to pixels that are not part of a polyp edge. In a more particular example, as described above in connection with FIG. 13, the set of training images can be divided by using a Canny edge detector, a ground truth approach, or any other suitable edge detection approaches. As also described above, the edge detection approach used to divide the training images into positive samples and negative samples can be selected based on a performance evaluation of the various approaches (e.g., an area under the receiver operating characteristic curve measurement).

In some embodiments, process 1700 can include obtaining training patches from each training image for training the convolutional neural network classifier at 1710. For example, as shown in FIG. 7, training images, such as training images 710, 720, and 730, can each have associated labels—e.g., y=0 for images having pixels that are not likely to contain a polyp edge and y=1 for images having pixels that are likely to contain a polyp edge. As shown in FIG. 8, each training image can be divided into any suitable number of N patches. For example, in FIG. 8, training image 710 has been divided into nine training patches. Each of these training patches can be modified using any suitable approach, such as modification by scale, modification by translation, modification by rotation or flipping, etc. For example, a set of 32×32 oriented training patches can be obtained at varying scales.

Accordingly, each training image having a polyp edge label can be used to obtain multiple training patches with the same polyp edge label. For example, for a training image with y=1, each of the multiple training patches having the same label ($y_i$=1, =1, 2, 3, . . . , N) can be generated. This can, for example, increase the dataset of training images used to train the convolutional neural network classifier.

It should be noted that, in some embodiments, the obtained training patches can be resized to a particular size (e.g., 28×28, 32×32, etc.).

Referring back to FIG. 17, the convolutional neural network classifier can then be trained using the obtained training patches at 1720. It should be noted that the convolutional neural network classifier can be composed of multiple layers having any suitable number of convolution steps and any suitable number of subsampling steps.

In a more particular example, the convolutional neural network classifier used to classify whether a polyp edge is present in an image can include four layers including two convolution steps and two subsampling steps. The first layer can convolve the original images with six filters of size 5×5, followed by subsampling the resulting images to reduce their size by half. Treating the resulting images as its input, the third layer of the convolutional neural network classifier can convolve these images with twelve filters of size 5×5, followed by again subsampling the resulting images to reduce their size by half.

In some embodiments, in addition to the network architecture, other input parameters to the convolutional neural network classifier can include alpha, batch size, and the number of epochs. Generally speaking, alpha can be used to define the learning rate of the convolutional neural network classifier, batch size can specify the number of images to be used in each iteration, and the number of epochs can denote the number of full passes to perform through the entire dataset.

Referring back to FIG. 16, process 1600 can continue by testing the convolutional neural network classifier with a test image that generates a polyp edge label or a non-polyp edge label for association with the test image. In particular, process 1600 localizes polyp edges by applying the trained convolutional neural network classifier through scanning the test image. This is described further in connection with FIG. 18.

Figure 18:
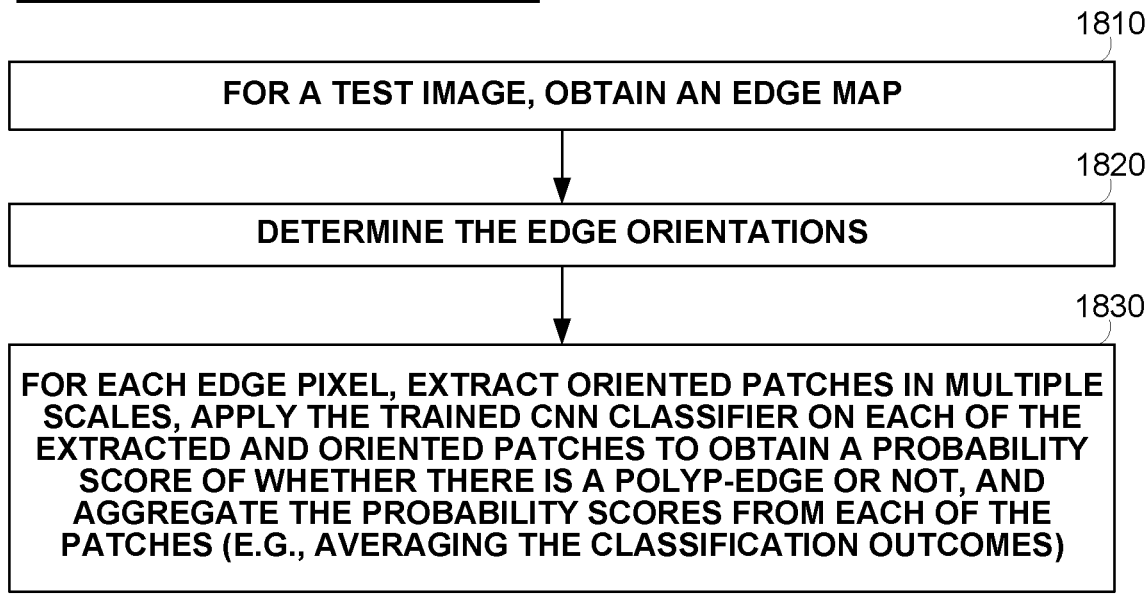
FIG. 18 is an illustrative example of a process for testing the convolutional neural network classifier described in FIG. 16 in accordance with some embodiments of the disclosed subject matter.

Turning to FIG. 18, process 1800 can include receiving a test image and then obtaining an edge map for the test image at 1810 and edge orientations can be computed at 1820. For each edge pixel, process 1800 can extract oriented patches in multiple and varying scales, apply the trained convolutional neural network classifier on each patch, and aggregate the classification results from each patch by averaging the classification outcomes over the number of patches.

In some embodiments, similar to the generation of training patches described above, oriented patches can be extracted from portions of the test image containing an edge pixel. In some embodiments, additional oriented patches can be obtained by modifying the scale of the original oriented patches. It should be noted that, in some embodiments, the oriented patches can be resized such that each oriented patch is the same size as the training patches obtained from the training images (e.g., 28×28, 32×32, etc.).

The trained convolutional neural network classifier can then be applied to each of the oriented patches, where a polyp edge probability score can be determined for each of the oriented patches. The polyp edge probability scores for each of the oriented patches can be aggregated to generate an aggregate polyp edge probability score. This aggregated probability score can, for example, be used to determine whether the test image is associated with a pixel edge label or a non-pixel edge label. For example, in response to the aggregate probability score for the test image being greater than 51%, the test image can be associated with a label indicating that the test image includes pixels is likely to have a pixel edge.

It should be noted that, in some embodiments, classification thresholds, such as the aggregate probability score needed to be deemed as containing a pixel edge, can be set by an operator of the quality monitor system.

In some embodiments, as described above, the polyp detector can evaluate the performance of the convolutional neural network classifier. For example, based on the aggregate probabilistic output from the convolutional neural network classifier and the ground truth of the testing images, the performance of the convolutional neural network classifier can be evaluated by reviewing the area under the receiver operating characteristic (ROC) curve. The area under the receiver operating characteristic curve measurements can be used to determine performance of the convolutional neural network classifier using different batch sizes and/or different numbers of epochs. Accordingly, the batch size and/or the number of epochs for constructing the convolutional neural network classifier can be selected based on the receiver operating characteristic curves and the associated area under receiver operating characteristic curve measurements.

In some embodiments, the polyp detector can use the performance evaluation data to select between machine learning classifiers. For example, in some embodiments, the polyp detector can use the performance evaluation data to select between using a random forest classifier and a convolutional neural network classifier on a colonoscopic video having multiple image frames.

It should be noted that the output of the polyp edge classification approaches described above can reduce the search space for polyps based on those pixels classified as likely to include a polyp edge. For example, a random forest classifier can be selected that was trained using a Canny edge detector without sampling, which can be used to determine pixels that are likely to include a polyp edge.

Referring back to 1250 of FIG. 12, the polyp detector can then find polyp candidates and use a machine learning classifier, such as a convolutional neural network classifier, for polyp classification—i.e., whether an image includes a polyp or a non-polyp. More particularly, based on the result of this classification that distinguishes between polyp edges and non-polyp edges (e.g., using the random forest classifier or the convolutional neural network classifier), the polyp detector can detect the likelihood that a polyp is present. For example, the polyp detector can apply a Hough transform on refined edge maps reconstructed from the classification output (e.g., what pixels include a polyp edge), where the detected circles from the Hough transform can serve as the basis for constructing polyp candidates or patches from each image. Candidate images of potential polyps can then be passed to a convolutional neural network classifier, which allows the convolutional neural network classifier to identify features and train the classifier for distinguishing between polyps and non-polyps. The convolutional neural network classifier can generate features through a number of convolution and subsampling layers such that the convolutions can produce feature maps of edges and lines in images and the subsampling can reduce image resolution and size. These feature maps can then be used to train the classifier.

Figure 19:
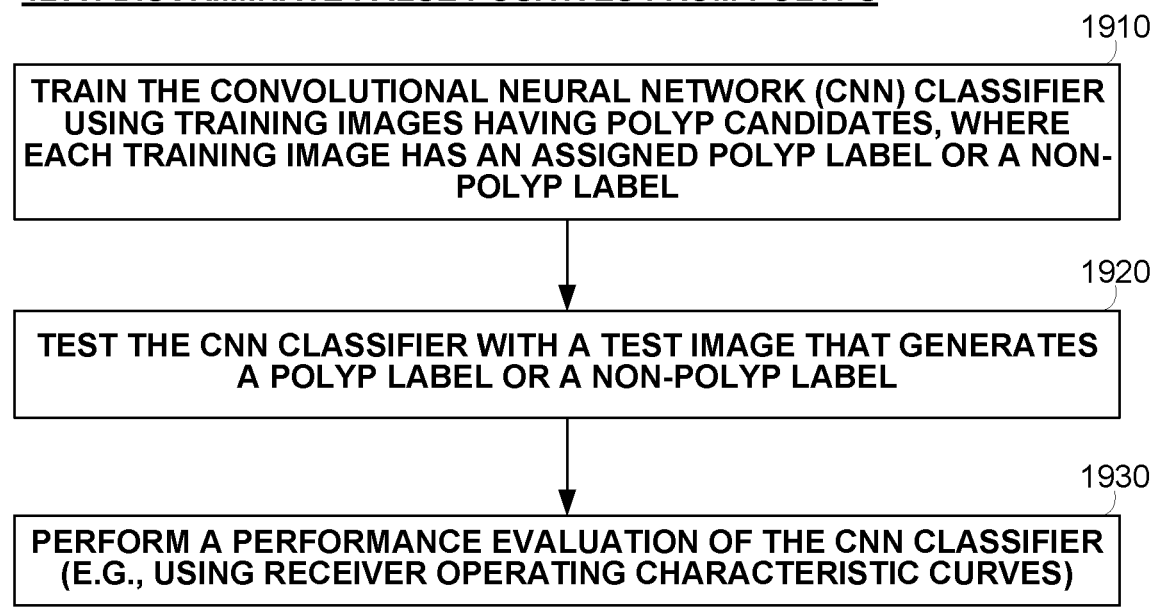
FIG. 19 is an illustrative example of a process for implementing an automatic polyp detector that can identify true polyps while sustaining a low false positive rate using a convolutional neural network classifier, where the classifier generates a polyp label or a non-polyp label, in accordance with some embodiments of the disclosed subject matter.

Turning to FIG. 19, FIG. 19 shows an illustrative example of a process 1900 for implementing an automatic polyp detector that can identify true polyps while sustaining a low false positive rate using a convolutional neural network classifier, where the classifier generates a polyp label or a non-polyp label, in accordance with some embodiments of the disclosed subject matter. As shown, process 1900 begins by training the convolutional neural network classifier using training images having polyp candidates at 1910, where each training image has an assigned polyp label or a non-polyp label. This is further described in connection with FIG. 20.

Figure 20:
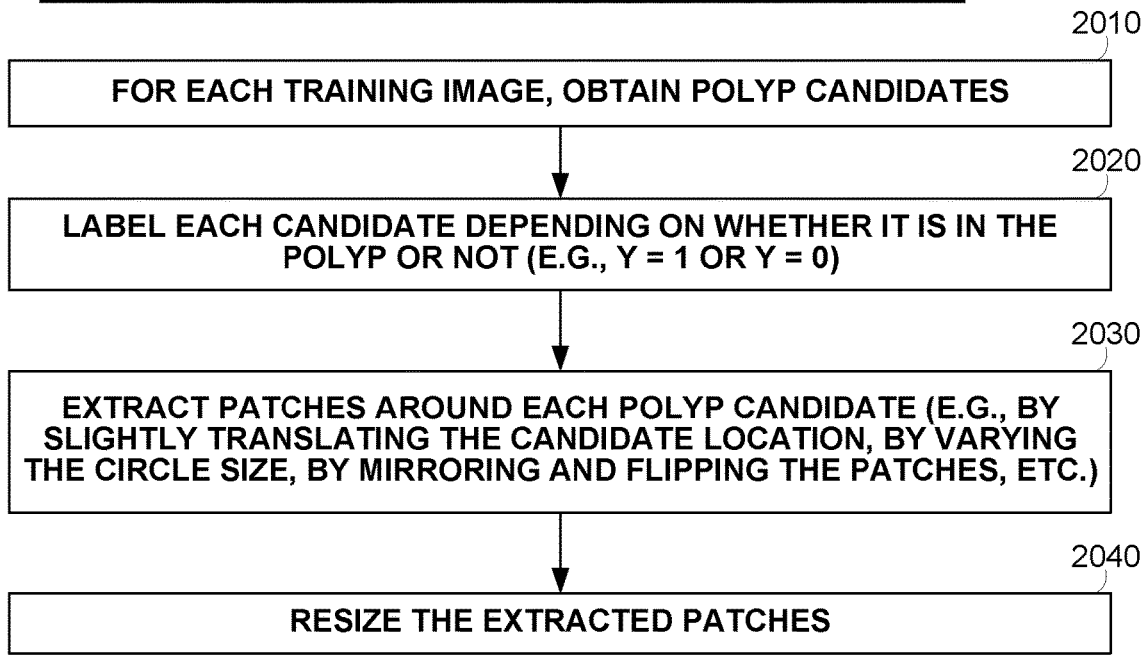
FIG. 20 is an illustrative example of a process for training the convolutional neural network classifier described in FIG. 19 in accordance with some embodiments of the disclosed subject matter.
Figure 21:
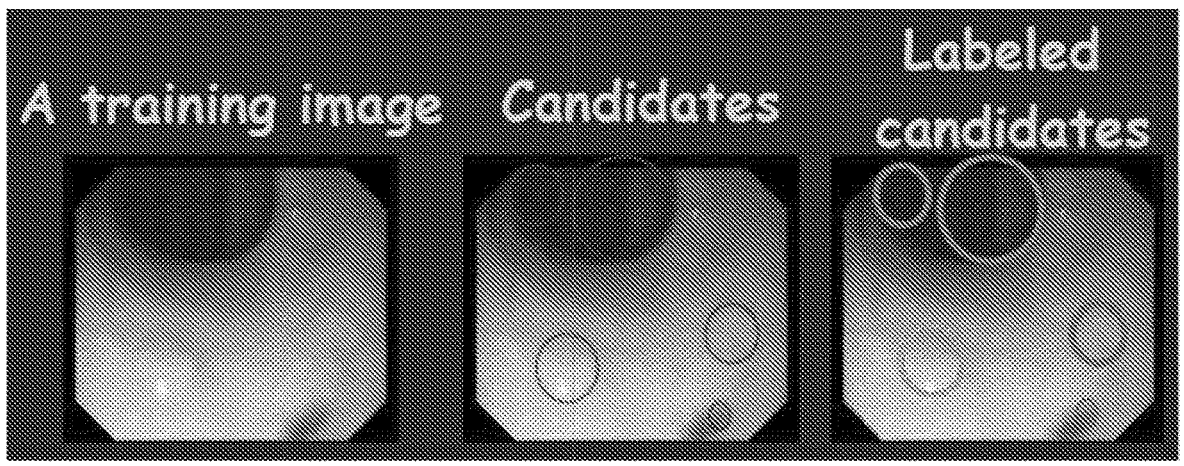
FIG. 21 is an illustrative example of a training image, a set of polyp candidates, and a set of labeled polyp candidates in accordance with some embodiments of the disclosed subject matter.

As shown in FIG. 20, polyp candidates can be obtained from each training image at 2010. This can include creating a refined edge map by, for example, passing training features to the trained random forest model, which can be followed by generating edge maps include those pixels classified as polyp edges. This can, for example, identify fewer pixels as compared to other edge detection approaches in that it focuses on pixels that are likely to be part of polyp edges. Upon creating these refined edge maps, a circular Hough transform can be applied on these edge maps. The detected circles from the Hough transform can form polyp candidates. An illustrative example of a training image and a set of unlabeled polyp candidates is shown in FIG. 21.

At 2020, upon obtaining polyp candidates, the polyp detector can label each candidate depending on whether the candidate is in the polyp or not. More particularly, polyp candidates or the image patches described below can be labeled using the centers of the detected circles, where polyp candidates or image patches created from circles having centers falling within the boundaries of the ground truth image can be labeled as positive (or being in the polyp) and polyp candidates or image patches created from circles having centers falling outside the boundaries of the ground truth image can be labeled as negative (or not being in the polyp). For example, a label of y=1 can be applied upon determining that the candidate is in the polyp and a label of y=0 can be applied upon determining that the candidate is not in the polyp. An illustrative example of a training image, the training image including a set of unlabeled polyp candidates (e.g., after applying the circular Hough transform), and the training image including a set of labeled polyp candidates is shown in FIG. 21.

At 2030, based on the detected circles from the Hough transform, image patches can be extracted in various scales from the corresponding original images using the centers and radii of the detected circles. For example, patches around each polyp candidate can be extracted by translating the candidate location, varying the size of the detected circle, and/or mirroring and flipping the patches.

In a more particular example, eight total patch versions can be generated by rotating the original patch containing the polyp candidate by 90 degrees, 180 degrees, and 270 degrees, followed by obtaining the mirror image of each by flipping each image patch horizontally. In some embodiments, scaling can be performed in order to, for example, capture a portion of the area surrounding polyps in polyp patches. In some embodiments, rotating and flipping each patch can be performed in order to, for example, train the convolutional neural network classifier to recognize polyps in various orientations.

Figure 22:
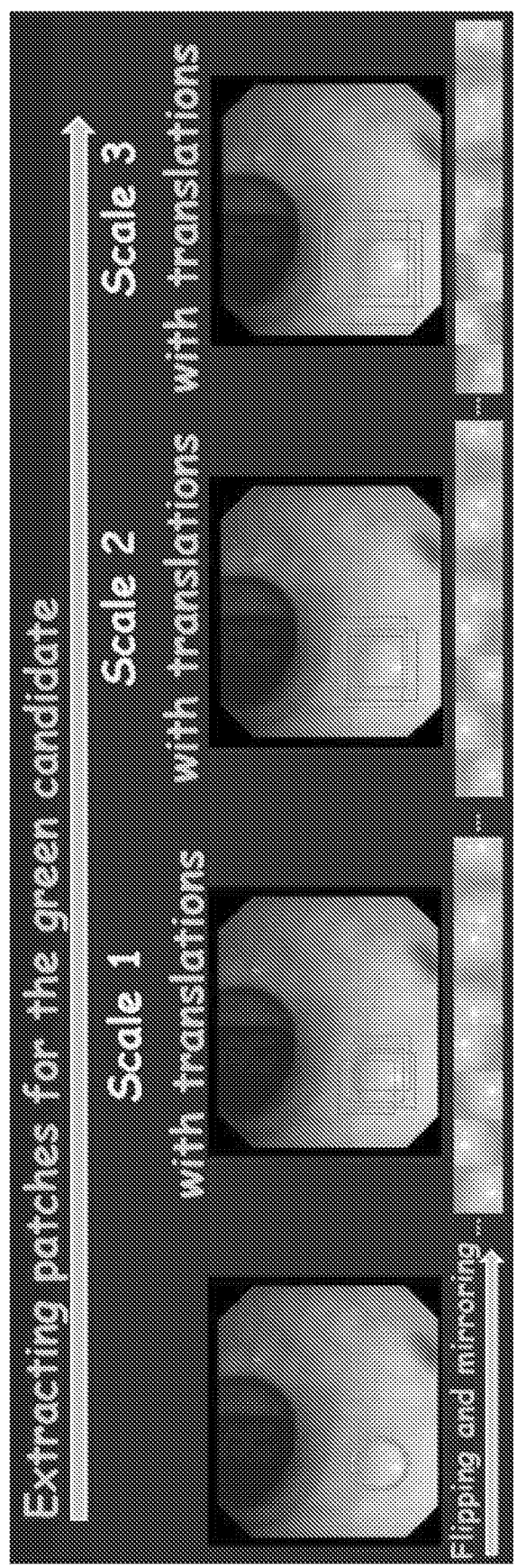
FIG. 22 is an illustrative example of a process for extracting image patches in various scales from a polyp candidate in accordance with some embodiments of the disclosed subject matter.

In another more particular example, image patches can be generated with different scales and/or translations. For example, a first scale can be selected as a square of size $s1=2\times R$, where R is the radius of the circle given by the application of the Hough transform. In continuing this example, a second scale can be selected as a square of size $s2=1.2\times s1$ and a third scale can be selected as a square of size $s3=1.2\times s2$. Each of these patches can then be translated in any number of random directions (e.g., with a small translation magnitude). An illustrative example of the extracted image patches in various scales, various rotations, and various orientations is shown in FIG. 22.

In some embodiments, prior to transmitting the extracted image patches or polyp candidates to the convolutional neural network classifier, the image patches can be resized to a particular size (e.g., 32×32, 64×64, etc.).

These extracted image patches and/or polyp candidates can be transmitted to the convolutional neural network classifier to train the classifier.

In some embodiments, a convolutional neural network classifier can be implemented having any suitable number of layers. For example, the convolutional neural network classifier can be constructed to include four layers—e.g., two convolution layers interleaved with two subsampling layers. In this example, a first convolution layer can include six filters of size 5×5 followed by a subsampling layer that can reduce the size of the resulting images by half. The second convolution layer can include twelve filters of size 5×5 for convolving with the images from the result of the previous subsampling layer, which can be followed by a subsampling layers that again reduces the resulting images by half.

In another more particular example, the convolutional neural network classifier can be constructed to include size layers—e.g., three convolution layers interleaved with three subsampling layers. In this example, a subsampling layer followed each convolution layer and was used to reduce the size of the images resulting from the previous layer by half. In continuing this example, the first convolution layer included six filters of size 9×9, the second convolution layer included twelve filters of size 5×5, and the third convolution layer included twenty-four filters of size 5×5. In addition, the convolutional neural network classifier can be set to include an alpha parameter that represents the learning rate of the network, where a value of 1 was used for the alpha parameter to denote a constant learning rate.

Figure 23:
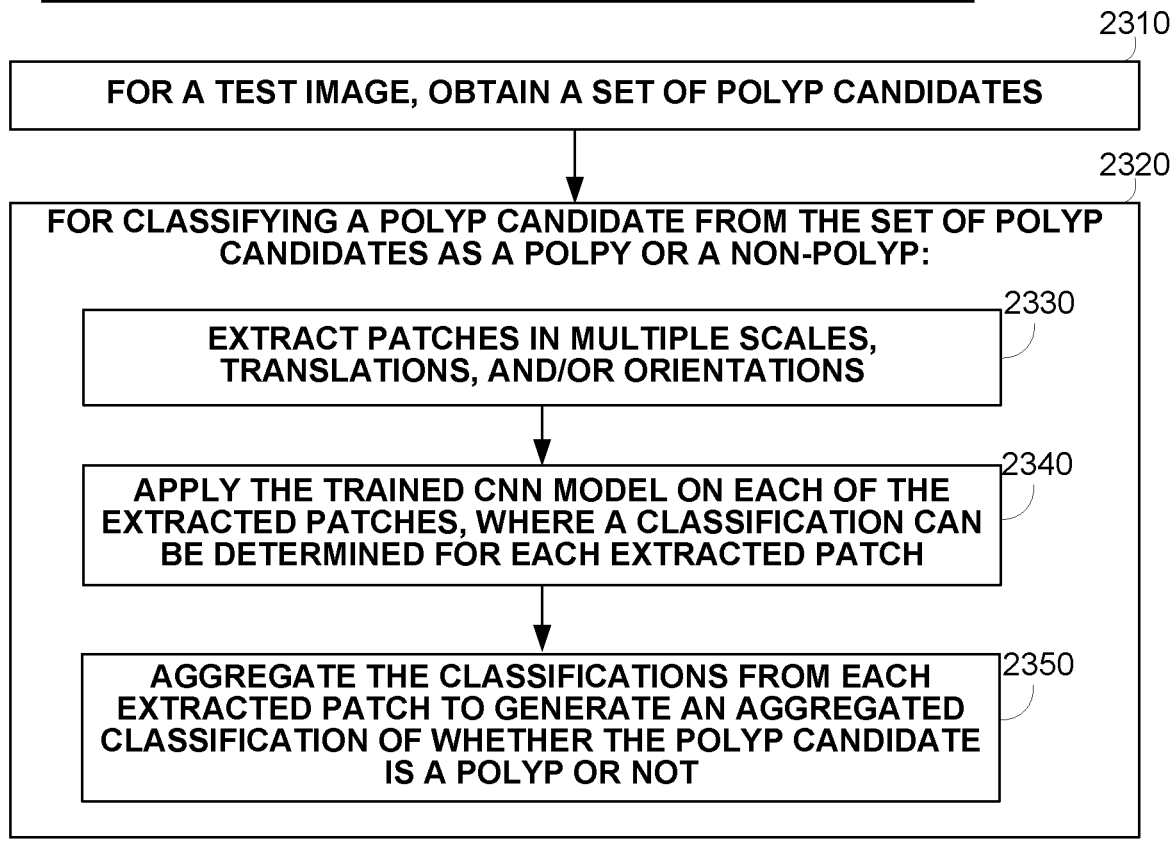
FIG. 23 is an illustrative example of a process for testing the convolutional neural network classifier described in FIG. 19 in accordance with some embodiments of the disclosed subject matter.

Referring back to FIG. 19, process 1900 begins by testing the convolutional neural network classifier to determine a polyp label or a non-polyp label for association with a received test image. This is further described in connection with FIG. 23. As shown in FIG. 23, testing the convolutional neural network classifier includes obtaining polyp candidates from the received test image at 2310 and classifying each of the polyp candidates from the test image as being a polyp (or polyp-like structure) or a non-polyp and 2320.

For example, similar to the approach for training the convolutional neural network classifier described above, testing the convolutional neural network classifier can include receiving a test image and then obtaining a refined edge map for the test image using the previously trained machine learning classifier to determine pixels likely to contain a polyp edge. Upon obtaining a refined edge map, a Hough transform can be applied to the edge map to obtain candidate polyps at 2310.

From the candidate polyps, multiple patches can be extracted in varying scales, translations, and/or orientations similar to the training patches described above at 2330. It should be noted that, in some embodiments, the extracted patches can be resized to a particular size (e.g., 32×32, 64×64, etc.). These extracted patches can be transmitted to the trained convolutional neural network classifier at 2340, where the classifier can determine, for each patch, a polyp classification score that indicates the likelihood that the patch contains a polyp.

At 2350, the polyp classification scores for each patch can be aggregated to generate an aggregated polyp classification score. For example, an average of the classification outcomes over the multiple patches can be calculated as the aggregated polyp classification score. In another example, particular patches can be weighted in any suitable approach (e.g., patches having a greater informativeness score can be weighted higher, patches occurring in a particular portion of the colon can be weighted higher, etc.). This aggregated probability score can, for example, be used to determine whether the test image is associated with a polyp label or a non-polyp label. For example, in response to the aggregate probability score for the test image being greater than 51%, the test image can be associated with a label indicating that the test image contains a polyp. That is, a polyp can be deemed to be detected based on the aggregated polyp classification score.

Referring back to FIG. 19, in some embodiments, the polyp detector can evaluate the performance of the convolutional neural network classifier for differentiating between polyp candidates having a polyp and not having a polyp. For example, based on the aggregate probabilistic output from the convolutional neural network classifier and the ground truth of the testing images, the performance of the convolutional neural network classifier can be evaluated by reviewing the area under the receiver operating characteristic (ROC) curve. The area under the receiver operating characteristic curve measurements can be used to determine performance of the convolutional neural network classifier using different batch sizes and/or different numbers of epochs. Accordingly, the batch size and/or the number of epochs for constructing the convolutional neural network classifier can be selected based on the receiver operating characteristic curves and the associated area under receiver operating characteristic curve measurements.

Figure 24:
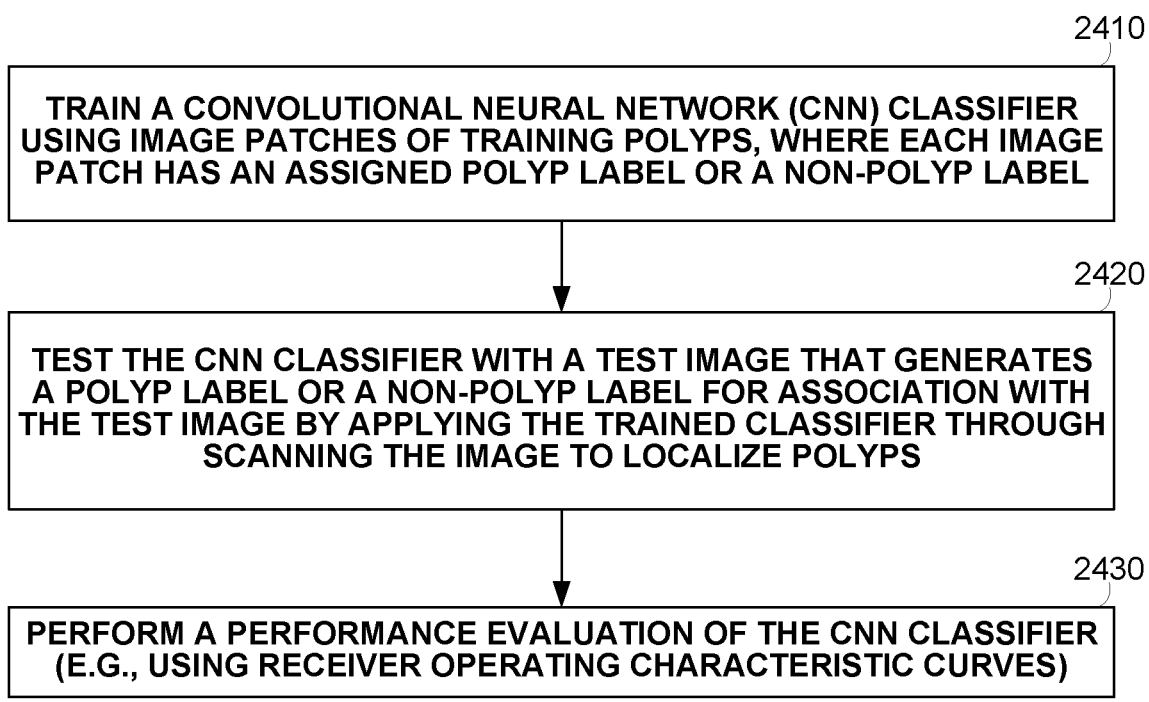
FIG. 24 is an illustrative example of a process for implementing a polyp detector with a convolutional neural network classifier using sliding windows in accordance with some embodiments of the disclosed subject matter.

Additionally or alternatively, in some embodiments, the polyp detector can localize polyps directly with a convolutional neural network classifier using sliding windows. As shown in FIG. 24, similar to FIG. 19, the convolutional neural network classifier can be constructed by training the convolutional neural network classifier using image patches from training images at 2410, where each image patch is associated with a polyp label or a non-polyp label, testing the convolutional neural network classifier with a test image that generates a polyp classification label by applying the trained classifier through scanning the image using sliding windows at 2420, and performing a performance evaluation of the convolutional neural network classifier at 2430.

Figure 25:
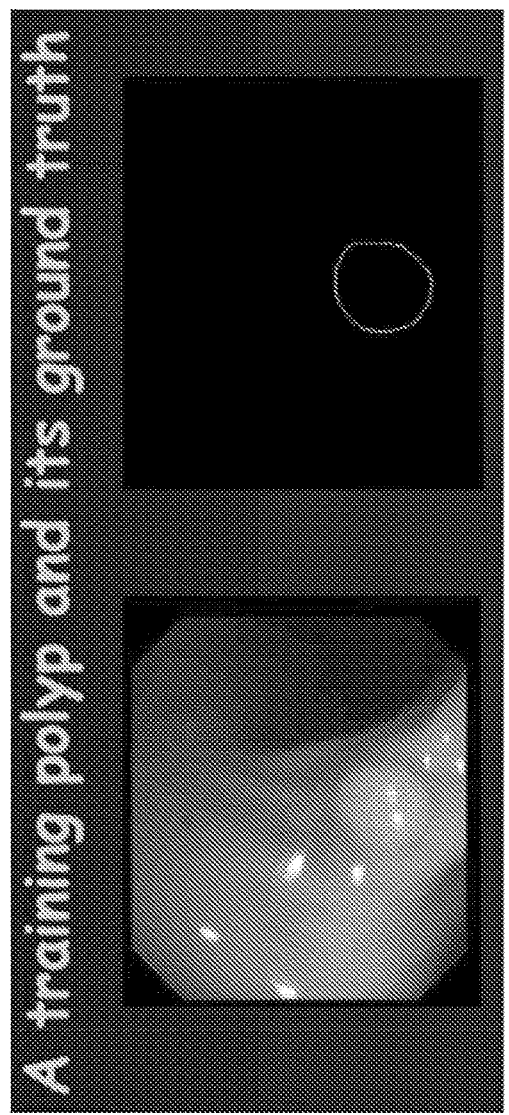
FIG. 25 is an illustrative example of a training polyp, a ground truth image associated with the training polyp, and multiple image patches extracted from the polyp based on the ground truth image in accordance with some embodiments of the disclosed subject matter.
Figure 25:
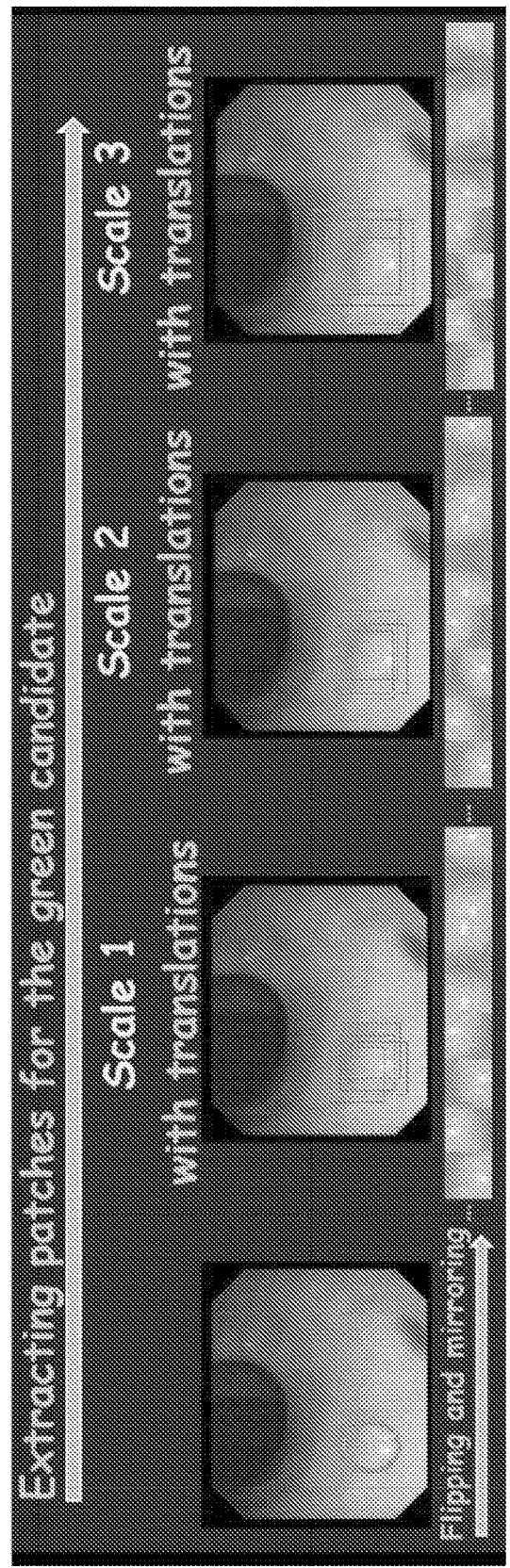

It should be noted that, additionally or alternatively to the training of the convolutional neural network classifier described in connection with FIG. 19, the polyp detector can train the convolutional neural network classifier using patches obtained from one or more training polyps. As shown in FIG. 25, multiple image patches can be extracted from a training polyp and its ground truth image. For example, patches can be extracted by translating the location around the training polyp, varying the size of the bounding box around the training polyp, and/or mirroring and flipping the patches.

In a more particular example, image patches can be generated with different scales and/or translations. For example, a first scale can be selected as a square of size s1=max (w,h), where w and h are the width and height of the bounding box of the polyp in the ground truth image. In continuing this example, a second scale can be selected as a square of size s2=1.2×s1 and a third scale can be selected as a square of size s3=1.2×s2. Each of these patches can then be translated in any number of random directions (e.g., with a small translation magnitude). An illustrative example of the extracted image patches in various scales, various rotations, and various orientations is shown in FIG. 25.

Using these image patches, the convolutional neural network classifier that determines a probability that a polyp is detected within an image can be trained.

It should be noted that, in some embodiments, the polyp detector can use the performance evaluation data to select between machine learning classifiers. For example, in some embodiments, the polyp detector can use the performance evaluation data to select between using a convolutional neural network classifier trained using one approach and a convolutional neural network classifier trained using a different approach.

In response to determining that the probability that a polyp is present in an informative image frame is greater than a polyp classification threshold, an alert or notification of the presence of the detected polyp can be presented. For example, as shown in FIG. 1C, in response to determining that the probability that an informative frame contains a polyp is greater than a predetermined probabilistic threshold, the informative image frame can be presented along with a bounding box or other indication showing a region of interest containing the detected polyp within the informative image frame. In a more particular example, bounding box can be presented around a detected polyp to an operator in response to the determined probability being greater than a particular classification threshold value, where the classification threshold value can be configured by the operator of the polyp detection system (e.g., place a bounding box when the probability that an image frame includes a polyp is greater than 60%).

It should be noted that, in some embodiments, the informative image frame with the detected polyp with a region or bounding box can be presented with any other suitable information to assist the user performing the procedure, such as the informativeness score for the image frame, a polyp probability score determined using one or more machine learning techniques, polyp location information, image frame information, video information, polyp shape information, polyp size information, polyp color information, polyp property information, etc. It should also be noted that the type of information presented along with the informative image frame and the bounding box can be configured by the operator of the polyp detection system.

This can, for example, direct the attention of the endoscopist towards a detected polyp, thus increasing endoscopist attentiveness and reducing polyp miss rates.

Figure 26:
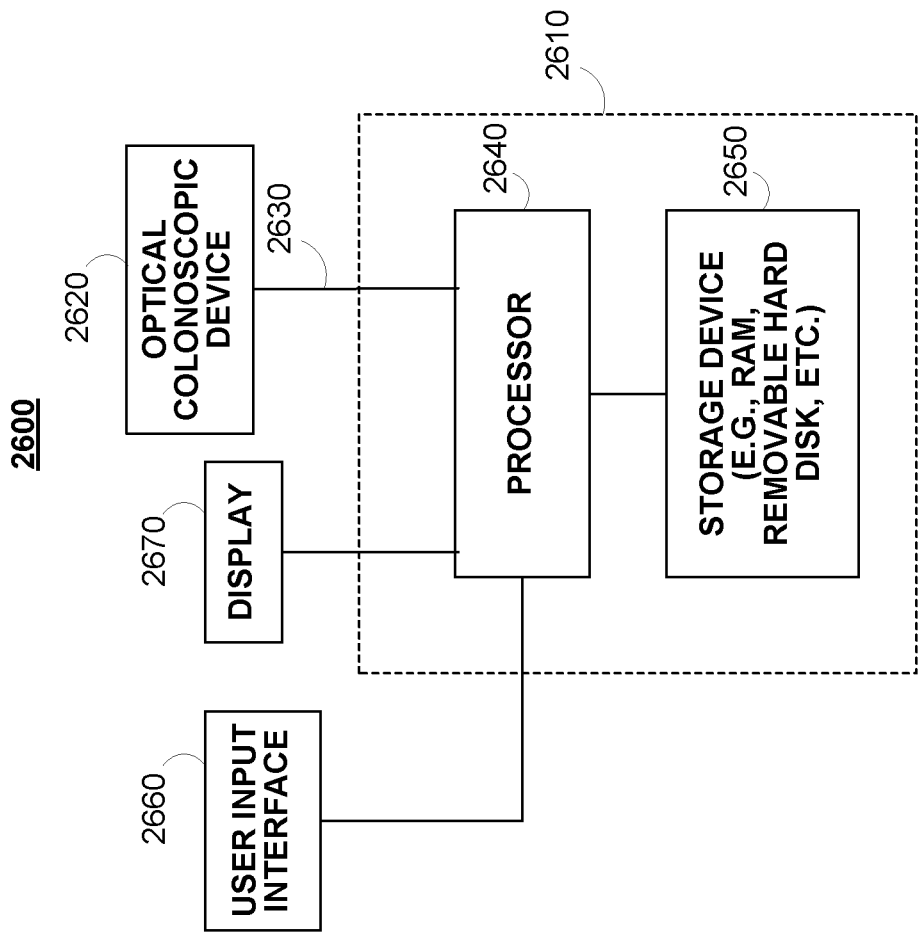
FIG. 26 is an illustrative system for simultaneously monitoring colonoscopic video quality and detecting polyps in colonoscopy in accordance with some embodiments of the disclosed subject matter.

Turning to FIG. 26, FIG. 26 shows a generalized embodiment of an illustrative system 2600 for simultaneously monitoring colonoscopic video quality and detecting polyps in colonoscopy in accordance with some embodiments of the disclosed subject matter. As shown, the illustrative system 2600 includes a computing device 2610 and an optical colonoscopic device 2620. Computing device 2610 can be any suitable computing device for providing access to the mechanisms for simultaneously monitoring colonoscopic video quality and detecting polyps in colonoscopy described herein, such as a processor, a computer, a data processing device, or a combination of such devices. For example, the mechanisms for simultaneously monitoring colonoscopic video quality and detecting polyps in colonoscopy described wherein can be distributed into multiple backend components and multiple frontend components or interfaces. In a more particular example, backend components, such as data collection and data distribution can be performed on optical colonoscopic device 2620. In another more particular example, colonoscopic video and/or images can be obtained from optical colonoscopic device 2620 and transmitted to computing device 2610 via a data acquisition interface or any other suitable image acquisition hardware, while image processing performed by the quality monitor system and/or the automatic polyp detection system can be performed by computing device 2610. Similarly, the graphical user interfaces displayed by the mechanisms for simultaneously monitoring colonoscopic video quality and detecting polyps in colonoscopy described herein, such as interfaces for displaying colonoscopic videos or images contained therein, interfaces for providing quality and/or informativeness information or notifications, and interfaces for providing automatic polyp detection information, can be distributed by one or more computing devices 2610.

Optical colonoscopic device 2620 can, for example, be any suitable image device for performing a colonoscopy procedure. Computing device 2620 can interface with optical colonoscopic device 2620 via image acquisition hardware that can be configured to acquire optical image data continuously or intermittently, for example, during a medical procedure, such as a colonoscopy, and relay optical image data for processing. The image acquisition hardware may require operator direction, input, or feedback, or may be designed to operate autonomously.

More particularly, for example, computing device 2610 can be any of a general purpose device such as a computer or a special purpose device such as a client, a server, etc. Any of these general or special purpose devices can include any suitable components such as a processor (which can be a microprocessor, digital signal processor, a controller, etc.), memory, communication interfaces, display controllers, input devices, etc. For example, computing device 2610 can be implemented as a personal computer, a tablet computing device, a personal data assistant (PDA), a portable email device, a multimedia terminal, a mobile telephone, a gaming device, a set-top box, a television, etc.

In some embodiments, any suitable computer readable media can be used for storing instructions for performing the processes described herein, can be used to determine carotid intima-media thickness, etc. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Referring back to FIG. 26, communications link 2630 (and other links described herein) may be any communications links suitable for communicating data between computing device 2610 and optical colonoscopic device 2620, such as network links, dial-up links, wireless links, hard-wired links, any other suitable communications links, or a combination of such links. Computing device 2610 enables a user to access features of the quality monitor system, the automatic polyp detection system, and the mechanisms for simultaneously monitoring colonoscopic video quality and detecting polyps in colonoscopy described herein. Computing device 1410 may be personal computers, laptop computers, mainframe computers, dumb terminals, data displays, Internet browsers, personal digital assistants ("PDAs"), two-way pagers, wireless terminals, portable telephones, any other suitable access device, or any combination of such devices. Computing device 2610 and optical colonoscopic device 2620 may be located at any suitable location. In one embodiment, computing device 2610 and optical colonoscopic device 2620 may be located within an organization. Alternatively, computing device 2610 and optical colonoscopic device 2620 may be distributed between multiple organizations.

It should also be noted that computing device 2610 can include processor 2640, memory 2650, input device 2660, and display 2670, which may be interconnected. In some embodiments, memory 2650 contains a storage device for storing a computer program for controlling processor 2640.

Processor 2640 uses the computer program to present on display 2670 interfaces, notifications, and other features of the quality monitor system, the automatic polyp detection system, and the mechanisms for simultaneously monitoring colonoscopic video quality and detection polyps in colonoscopy and the data received through communications link 2630 and commands and values transmitted by a user of computing device 2610. It should also be noted that data received through communications link 2630 or any other communications links may be received from any suitable source. Input device 2660 may be a computer keyboard, a mouse, a cursor-controller, dial, switchbank, lever, or any other suitable input device as would be used by a designer of input systems or process control systems. Alternatively, input device 2660 may be a finger or stylus used on a touch screen display 2670.

In some embodiments, the mechanisms for simultaneously monitoring colonoscopic video quality and detection polyps in colonoscopy may include an application program interface (not shown), or alternatively, the application may be resident in the memory of computing device 2610. In another suitable embodiment, the only distribution to computing device 2610 may be a graphical user interface ("GUI") which allows a user to interact with the mechanisms for simultaneously monitoring colonoscopic video quality and detection polyps in colonoscopy resident at, for example, another computing device.

In one particular embodiment, the mechanisms for simultaneously monitoring colonoscopic video quality and detection polyps in colonoscopy may include client-side software, hardware, or both. For example, the application may encompass one or more Web-pages or Web-page portions (e.g., via any suitable encoding, such as HyperText Markup Language ("HTML"), Dynamic HyperText Markup Language ("DHTML"), Extensible Markup Language ("XML"), JavaServer Pages ("JSP"), Active Server Pages ("ASP"), Cold Fusion, or any other suitable approaches).

Accordingly, methods, systems, and media for simultaneously monitoring colonoscopic video quality and detection polyps in colonoscopy are provided.

Although the invention has been described and illustrated in the foregoing illustrative embodiments, it is understood that the present disclosure has been made only by way of example, and that numerous changes in the details of implementation of the invention can be made without departing from the spirit and scope of the invention, which is only limited by the claims which follow. Features of the disclosed embodiments can be combined and rearranged in various ways.

What is claimed is:

1. A method for polyp detection in optical colonoscopic images, the method comprising:
receiving a plurality of image frames of a colonoscopic video in real time as a colonoscopy procedure is being performed; and
in real time while the plurality of image frames of colonoscopic video is being received:
applying, using a hardware processor, a first trained classifier to each image frame of the plurality of image frames, wherein the first trained classifier determines an informativeness score that indicates a likelihood that an image frame includes informative content based on at least one of whether the image frame is in-focus, whether the image includes a bubble, whether the image includes one or more light reflection artifacts, and whether the image is blurred, wherein the informativeness score indicates that the image frame is non-informative when the image frame includes a bubble;
wherein the first trained classifier is trained using images including a first image that includes one or more light reflection artifacts acid a second image that is not in-focus, includes a bubble, or is blurred;
presenting an interface that includes an image frame from the plurality of images, wherein the interface includes an indicator that represents the informativeness score of the image in the interface;
determining whether each image frame from the plurality of image frames is an informative image frame based on the informativeness score;
applying a second trained classifier to each informative image frame, wherein the second trained classifier determines a polyp detection score that indicates a likelihood that the informative image frame contains one or more polyps; and
presenting, in the interface, an indication that a polyp has been detected in the informative image frame.

2. The method of claim 1, wherein the first trained classifier is a random forest classifier that is trained based on extracted features from training images and clustering the extracted features to form visual words based on a bag of visual words model.

3. The method of claim 1, wherein the first trained classifier is a random forest classifier that is constructed based on histograms that represent the number of features belonging to each visual word in a bag of visual words model.

4. The method of claim 1, wherein the first trained classifier is a convolutional neural network classifier, wherein the convolutional neural network classifier divides the image frame into a plurality of regions, applies the convolutional neural network classifier to each of the plurality of regions to obtain a plurality of informativeness scores, aggregates the plurality of informativeness scores to obtain an aggregate informativeness score, and labels the image frame based on the aggregated informativeness score.

5. The method of claim 1, further comprising:
applying a third trained classifier to each informative image frame to classify which pixels in an informative image frame are likely to contain a polyp edge; and
generating an edge map based on the polyp edge classification information.

6. The method of claim 5, wherein a Canny edge detector is applied to each informative image frame to obtain a Canny edge map and wherein the generated edge map includes common pixels between the Canny edge map and a ground truth image corresponding to the informative image frame.

7. The method of claim 5, further comprising:
applying a Hough transform to the generated edge map to obtain a plurality of candidate polyps;
extracting image patches from the plurality of candidate polyps;
applying the second trained classifier to the extracted image patches, wherein the second trained classifier is a convolutional neural network classifier that classifies each of the extracted image patches to obtain a plurality of polyp classification scores;
aggregating the plurality of polyp classification scores to obtain air aggregate polyp score; and
labeling the informative image frame based on the aggregated polyp score.

8. The method of claim 1, further comprising presenting a second indicator in the interface that represents an average informativeness score over a subset of image frames.

9. The method of claim 1, wherein the presenting of the indication further comprises placing a bounding box in an area surrounding the detected polyp.

10. The method of claim 1, wherein the indicator is a visual indicator.

11. The method of claim 10, wherein the visual indicator is a bar indicator.

12. The method of claim 10, wherein the visual indicator is a traffic light indicator.

13. The method of claim 10, wherein the visual indicator indicates at least three informativeness score values.

14. The method of claim 1, wherein the first trained classifier trained using the images including the first image and the second image, further comprises:
the first trained classifier trained using the first image which is blurred; and
the first trained classifier trained using the second image that is not in-focus, in which the second image further includes one or more light reflection artifacts.

15. The method of claim 1, wherein the first trained classifier trained using the images including the first image and the second image, further comprises the first trained classifier trained using:
the first image that is not in-focus,
the second image that includes the bubble,
a third image that includes one or more light reflection artifacts, and
a fourth image that is blurred.

16. A system for polyp detection in optical colonoscopic images, the system comprising:
a hardware processor that is configured to:
receive a plurality of image frames of a colonoscopic video in real time as a colonoscopy procedure is being performed; and
in real time while the plurality of image frames of colonoscopic video is being received:
apply a first trained classifier to each image frame of the plurality of image frames, wherein the first trained classifier determines an informativeness score that indicates a likelihood that an image frame includes informative content based on at least one of whether the image frame is in-focus, whether the image includes a bubble, whether the image includes one or more light reflection artifacts, and whether the image is blurred, wherein the informativeness score indicates that the image frame is non-informative when the image frame includes a bubble;

wherein the first trained classifier is trained using images including a first image that includes one or more light reflection artifacts and a second image that is not in-focus, includes a bubble, or is blurred;

present an interface that includes an image frame from the plurality of images, wherein the interface includes an indicator that represents the informativeness score of the image in the interface;

determine whether each image frame from the plurality of image frames is an informative image frame based on the informativeness score;

apply a second trained classifier to each informative image frame, wherein the second trained classifier determines a polyp detection score that indicates a likelihood that the informative image frame contains one or more polyps;

and present, in the interface, an indication that a polyp has been detected in the informative image frame.

17. The system of claim 16, wherein the first trained classifier is a random forest classifier that is trained based on extracted features from training images and clustering the extracted features to form visual words based on a bag of visual words model.

18. The system of claim 16, wherein the first trained classifier is a random forest classifier that is constructed based on histograms that represent the number of features belonging to each visual word in a bag of visual words model.

19. The system of claim 16, wherein the first trained classifier is a convolutional neural network classifier, wherein the convolutional neural network classifier divides the image frame into a plurality of regions, applies the convolutional neural network classifier to each of the plurality of regions to obtain a plurality of informativeness scores, aggregates the plurality of informativeness scores to obtain an aggregate informativeness score, and labels the image frame based on the aggregated informativeness score.

20. The system of claim 16, wherein the hardware processor is further configured to:
apply a third trained classifier to each informative image frame to classify which pixels in an informative image frame are likely to contain a polyp edge; and
generate an edge map based on the polyp edge classification information.

21. The system of claim 20, wherein a Canny edge detector is applied to each informative image frame to obtain a Canny edge map and wherein the generated edge map includes common pixels between the Canny edge map and a ground truth image corresponding to the informative image frame.

22. The system of claim 20, wherein the hardware processor is further configured to:
apply a Hough transform to the generated edge map to obtain a plurality of candidate polyps;
extract image patches from the plurality of candidate polyps;
apply the second trained classifier to the extracted image patches, wherein the second trained classifier is a convolutional neural network classifier that classifies each of the extracted image patches to obtain a plurality of polyp classification scores;
aggregate the plurality of polyp classification scores to obtain an aggregate polyp score; and label the informative image frame based on the aggregated polyp score.

23. The system of claim 16, wherein the hardware processor is further configured to present a second indicator in the interface that represents an average informativeness score over a subset of image frames.

24. The system of claim 16, wherein the presenting of the indication further comprises placing a bounding box in an area surrounding the detected polyp.

25. The system of claim 16, wherein the indicator is a visual indicator.

26. The system of claim 25, wherein the visual indicator is a bar indicator.

27. The system of claim 25, visual indicator is a traffic light indicator.

28. The system of claim 25, wherein the visual indicator indicates at least three informativeness score values.

29. The system of claim 16, wherein the first trained classifier trained using the images including the first image and the second image, further comprises:
the first trained classifier trained using the first image which is blurred; and
the first trained classifier trained using the second image that is not in-focus, in which the second image further includes one or more light reflection artifacts.

30. The system of claim 16, wherein the first trained classifier trained using the images including the first image and the second image, further comprises the first trained classifier trained using:
the first image that is not in-focus,
the second image that includes the bubble,
a third image that includes one or more light reflection artifacts, and
a fourth image that is blurred.

31. Non-transitory computer-readable storage media, having computer-executable instructions stored thereupon that, when executed by a processor, the computer-executable instructions cause the processor to perform operations for polyp detection in optical colonoscopic images, wherein the operations include:
receiving a plurality of image frames of a colonoscopic video in real time as a colonoscopy procedure is being performed; and
in real time while the plurality of image frames of colonoscopic video is being received:
applying, using a hardware processor, a first trained classifier to each image frame of the plurality of image frames, wherein the first trained classifier determines an informativeness score that indicates a likelihood that an image frame includes informative content based on at least one of whether the image frame is in-focus, whether the image includes a bubble, whether the image includes one or more light reflection artifacts, and whether the image is blurred, wherein the informativeness score indicates that the image frame is non-informative when the image frame includes a bubble;
wherein the first trained classifier is trained using images including a first image that includes one or more light reflection artifacts and a second image that is not in-focus, includes a bubble, or is blurred;
presenting an interface that includes an image frame from the plurality of images, wherein the interface includes an indicator that represents the informativeness score of the image in the interface;

determining whether each image frame from the plurality of image frames is an informative image frame based on the informativeness score;

applying a second trained classifier to each informative image frame, wherein the second trained classifier determines a polyp detection score that indicates a likelihood that the informative image frame contains one or more polyps; and presenting, in the interface, an indication that a polyp has been detected in the informative image frame.

32. The non-transitory computer-readable medium of claim 31, wherein the indicator is a visual indicator.

33. The non-transitory computer-readable media of claim 32, wherein the visual indicator is a bar indicator.

34. The non-transitory computer-readable media of claim 32, wherein the visual indicator is a traffic light indicator.

35. The non-transitory computer-readable media of claim 32, wherein the visual indicator indicates at least three informativeness score values.

36. The non-transitory computer-readable media of claim 31, wherein the first trained classifier trained using the images including the first image and the second image, further comprises:
- the first trained classifier trained using the first image which is blurred; and
- the first trained classifier trained using the second image that is not in-focus, in which the second image further includes one or more light reflection artifacts.

37. The non-transitory computer-readable media of claim 31, wherein the first trained classifier trained using the images including the first image and the second image, further comprises the first trained classifier trained using:
- the first image that is not in-focus,
- the second image that includes the bubble,
- a third image that includes one or more light reflection artifacts, and
- a fourth image that is blurred.

\* \* \* \* \*